United States Patent [19]
Diel

[11] Patent Number: 6,103,459
[45] Date of Patent: Aug. 15, 2000

[54] COMPOUNDS FOR USE AS CHEMICAL VAPOR DEPOSITION PRECURSORS, THERMOCHROMIC MATERIALS LIGHT-EMITTING DIODES, AND MOLECULAR CHARGE-TRANSFER SALTS AND METHODS OF MAKING THESE COMPOUNDS

[75] Inventor: Bruce Diel, Overland Park, Kans.

[73] Assignee: Midwest Research Institute, Kansas City, Mo.

[21] Appl. No.: 09/264,733

[22] Filed: Mar. 9, 1999

[51] Int. Cl.[7] .................................................. G03C 1/85
[52] U.S. Cl. .......................... 430/530; 430/527; 430/529; 429/162; 429/191; 429/192; 429/194; 429/195; 252/62.2; 252/390; 252/395; 252/396; 252/500; 252/511; 252/512; 252/513; 252/514; 252/518
[58] Field of Search .................................. 430/530, 527, 430/529; 429/162, 191, 192, 194, 195; 252/511, 62.2, 390, 395, 396, 500, 512, 513, 514, 518

[56] References Cited

U.S. PATENT DOCUMENTS

| | | | |
|---|---|---|---|
| 4,081,313 | 3/1978 | McNeilly et al. | 156/610 |
| 4,368,098 | 1/1983 | Manasevit | 156/606 |
| 4,496,609 | 1/1985 | McNeilly et al. | 427/55 |
| 4,728,389 | 3/1988 | Logar | 156/612 |
| 5,894,656 | 4/1999 | Menon et al. | 29/623.1 |
| 5,897,813 | 4/1999 | Titomir et al. | 252/511 |
| 5,898,057 | 4/1999 | Chiang et al. | 528/71 |
| 5,900,182 | 5/1999 | Kanbara et al. | 252/62.2 |
| 5,902,518 | 5/1999 | Khazai et al. | 252/511 |
| 5,904,990 | 5/1999 | Stenger-Smith et al. | 428/457 |
| 5,905,021 | 5/1999 | Anderson et al. | 430/530 |

OTHER PUBLICATIONS

Krüger et al., "Über die Einwirkung von Natrium–bis–trimethylsilyl–amid auf Benzophenon, Benzaldehyd und Benzochinon[1])," *Techn. Hochschule Aachen*, pp. 2132–2137, 1963. This article discloses a ringed compound.

Roesky et al, "Cyclisierung von Bis(2,2,2–trifluorethoxy)–1,2–diiminoethan mit Schwefel–, Selen–, Phosphor–und Arsenchloriden," *Institut füur Anorganische Chemie der Universität Göttingen, Tammannstrasse*, vol. 39b, pp. 1315–1318, 1984. This article discloses a ringed compound having trifluorethoxy substituents.

Tuchtenhagen et al.,"Darstellung und Reaktionen von 1.2–Bis–trimethylsilyliminen," *Liebigs. Ann. Chem.*, vol. 711, pp. 174–183, 1968. This article discloses a number of ringed compounds.

Abernathy et al., "Chemical Perspectives of Microelectronic Materials III," *Materials Research Society Symposium Proceedings*, vol. 282, pp. 11–19, 1992.

Ashe, III et al., "Aromatic Antimony Compounds, Transition Metal Complexes of 2,5–dimethylstibacyclopentadienyl," *Journal of Organometallic Chemistry*, vol. 202 pp. C95–C98, 1980.

Ashe, III et al., "2,2',5'–Tetramethyldistibolyl. A. Thermochromic Distibine," *Journal of American Chemistry Society*, vol. 103, pp. 207–209, 1981.

Ashe, III et al., "Synthesis and Molecular and Crystal Structure of 2,2',5,5'–Tetramethylbiarsolyl," *Organometallics*, vol. 2, pp. 1005–1008, 1983.

Ashe, III et al., "2,2',5'–Tetramethyldistibolyl. A. Thermochromic Distibine," *Organometallics*, vol. 3, pp. 495–496, 1984.

Bertini et al., 1,2,5–Telluradiazole, $C_2H_2N_2Te$, *International Union Of Crystallography*, vol. C40, pp. 653–655, 1984.

Biefeld et al., "Effects of Growth Conditions and Substrate Orientation on the Properties Of InSb," *Materials Research Society Symposium Proceedings*, vol. 312, pp. 179–184.

Buchwald et al., "Synthese Und Reaktionen Von 1,2–Bis(t–rimethylsilyl)iminen," *Journal of Organometallic Chemistry*, vol. 166, pp. 25–30, 1979.

Chivers et al., Preparation, Crystal Structures, and Isomerization of the Tellurium Diimide Dimers $RNTe(\mu-NR')_2TeNR(R=R'={}^tBu; R=PPh_2NSiMe_3, R'={}^tBu, {}^tOct)$: X–ray Structure of the Telluradiazole Dimer $[{}^tBu_2C_6H_2N_2Te]_2$, *Inorganic Chemistry*, vol. 35, pp. 9–15, 1996.

Diel et al., "Synthesis, Characterization and Application of Main Group Element–containing 1,3,2–diazaheteroles in Materials Chemistry," SciFinder, Abstract, *Book of Abstracts*, 216th ACS National Meeting, Boston, Aug. 23–27 (1998).

Diel et al., "Synthesis, Characterization of the First Example of 1,3,2–diazaheterole Ring Compounds," SciFinder, Abstract, *Book of Abstracts*, 215th ACS National Meeting, Dallas, Mar. 29–Apr. 2 (1998).

Doppelt, "Copper CVD Precursors and Processes for Advanced Metallization," *Microelectronic Engineering*, vols. 37/38, pp. 89–95, 1997.

Girolami et al., "Tailored Organometallics as Low–temperature CVD Precursors to Thin Films," *Materials Research Society Symposium Proceedings*, vol. 121, pp. 429–438, 1988.

Jones et al., "Chemical Approaches to the Metalorganic CVD of Group–III Nitrides," *Journal of Chemical Vapor Deposition*, vol. 1, No. 3, pp. 65–73, 1995.

Karady et al., "1,2,5–thiadiazole–1–oxides.I.Synthesis and Reactions of Alkyoxy and Alkylthio Analogs," *Hetrocycles*, vol. 16, No. 9, pp. 1561–1568, 1981.

Matsuda et al., "Cyclization Reactions by the Use of 1,2–bis(trimethylsilyl)imino–1,2–diphenylethane," SciFinder, Abstract, *Chem. Lett.*, Issue 12, pp. 1457–1460, (1977).

(List continued on next page.)

*Primary Examiner*—Terressa M. Boykin
*Attorney, Agent, or Firm*—Shook, Hardy & Bacon LLP

[57] ABSTRACT

Novel compounds that may be used as chemical vapor deposition precursors, thermochromic materials, conductive polymers, light-emitting diode precursors, and molecular charge-transfer salt precursors are provided. In addition, a novel compound that can be used to make the aforementioned compounds is provided. Still further, another aspect of the present invention is to provide methods for making and using the novel compounds provided.

23 Claims, No Drawings

OTHER PUBLICATIONS

Motojima et al., "Single Crystal Growth by Chemical Vapor Deposition and Morphology of Binary and Ternary Compounds," *Journal of Chemical Vapor Deposition*, vol. 1, pp. 87–129, 1992.

Neidlein et al., "Reactions of 1,2–bis(Trimethylsilyl)imines with Selenium and Tellurium Halides," SciFinder, Abstract, *Fed. Rep. Ger. Helv. Chim. Acta*, vol. 70(4), pp. 1076–1078, (1987).

Neumayer et al., "Growth of Group III Nitrides. A Review of Precursors and Techniques," *Chemical Materials*, vol. 8, pp. 9–25, 1996.

O'Brien, "Chemical Considerations in the Design and Use Of Precursors for the Deposition of II/VI Materials by MOCVD and Related Methods," *Chemtronics*, vol. 5, pp. 61–70, 1991.

O'Brien et al., "Precursor Chemistry: Remaining Challenges and Some Novel Approaches," *Journal of Crystal Growth*, vol. 170, pp. 23–29, 1997.

Srivastava, "Synthesis of Te–N and Te–Te Bonded Compounds," *J. Indian Chem. Soc.*, vol. 74(9), pp. 709–710 (1997).

Sundermeyer et al., "Synthesis of New Unsaturated 16–membered Heterocyle With Alternating Carbon–carbon and Nitrogen–sulfer Building Blocks," SciFinder, Abstract, *Can. J. Chem.*, vol. 67(11), pp. 1785–1787, (1989).

Tuchtenhagen et al., "Silicon–nitrogen Bond. XXVI. Preparation and Reactions of 1,2–bis(trimethylsilylimines)," SciFinder, Abstract, *Justus Liebigs Ann. Chem.*, vol. 711, pp. 174–183, (1968).

Weidenbruch et al., "1,3,2–Diazasiloles by Silylene Addition to Trifluoroacetonitrile [1]," *Z. Anorg. Allg. Chem.*, vol. 622, pp. 1811–1813, 1996.

Zanella et al., "Organometallic Precursors in the Growth of Epitaxial Thin Films of Groups III–V Semiconductors by Metal–Organic Chemical Vapor Deposition," *Chemical Material*, vol. 3, pp. 225–242, 1991.

Zinn et al., "Reaction Pathways in Organometallic Chemical Vapor Deposition (OMCVD)," *Advanced Materials*, vol. 4, No. 5, pp. 375–378, 1992.

COMPOUNDS FOR USE AS CHEMICAL VAPOR DEPOSITION PRECURSORS, THERMOCHROMIC MATERIALS LIGHT-EMITTING DIODES, AND MOLECULAR CHARGE-TRANSFER SALTS AND METHODS OF MAKING THESE COMPOUNDS

STATEMENT REGARDING FEDERALLY-SPONSORED RESEARCH OR DEVELOPMENT

The government has certain rights in this invention.

CROSS REFERENCE TO RELATED APPLICATIONS

Not applicable.

BACKGROUND OF THE INVENTION

The present invention relates to certain novel chemical compounds. These compounds are useful as precursors for the chemical vapor deposition of thin films, thermochromic materials, conductive polymers, light-emitting diodes, and molecular charge-transfer salts.

Chemical vapor deposition is a process where thin films of elements are deposited on substrates by using volatile precursors. The precursors are heated to high temperatures, usually over 1000° C., where they vaporize and release a desired element on a substrate. The disadvantage with conventional precursors is that they must be heated to extremely high temperatures. Another disadvantage with conventional precursors is that they deposit unwanted elements on the substrate in addition to depositing the desired element.

An article by Sandor Karady et al. entitled 1,2,5-Thiadiazole-1-Oxides. I. Synthesis and Reactions of Alkoxy and Alkythio Analogs,- in *Heterocycles*, Vol. 16, No. 9, pp. 1561–1568, (1981), discloses a compound of the formula:

(A)

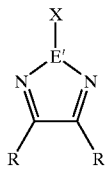

where E'=S, X=nothing or O, and R alkoxy, S-R, aminoalkyl, or aminoaryl.

An article by V. Bertini et al., entitled 1,2,5-Telluradiazole, $C_2H_2Te$ in *Acta Crystallography*, C40, pp. 653–655, (1984), discloses a similar compound to that disclosed by Karady et al. This compound is a compound of formula A where E'=Te, X=nothing, and R=H.

A similar compound is also disclosed in an article by Tristram Chivers et al., entitled Preparation, Crystal Structures, and Isomerization of the Telurium Diimide Dimers $RNTe(\mu NR')_2TeNR(R-R'-{}^tBu; R=PPh_2NSiMe_3, R'={}^tBu, {}^tOct)$: X-ray Structure of the Telluradiazole Dimer [${}^tBu_2CH_2N_2Te]_2$, in *Inorganic Chemistry*, Vol. 35, No. 1, pp. 9–15, (1996). This compound has the structure of formula A where E'=Te, X=nothing, and R=a fused conjugated ring.

In addition, a compound of formula A is disclosed in an article by Herbert W. Roesky et al., entitled Cyclisation of Bis(2,2,2-trifluoroethoxy)-1,2-diiminoethane with Sulfur, Selenium, Phosphorus, and Arsenic Chlorides, in Z. *Naturforsch.*, pp. 1315–1318 For this compound, R=trifluoroethoxy, and X=Cl when E'=P or As; X=nothing when E'=Se; and X=O or nothing when E'=S.

Still further, an article by H. Buchwald et al., entitled Synthese Und Reaktionen Von 1,2-Bis(trimethylsilyl) iminen 2, in *Journal of Organomnetallic Chemistry*, Vol. 166, pp. 25–30, (1979), discloses a compound of formula A, where R=aryl, and E'=C($sp^2$) when X=O; E'=S when X=nothing or O; E'=Se when X=nothing; and E'=P when X=O and phenyl on the same molecule. This article also discloses a compound of formula B, shown below, which can be used to make compound A. The compound of formula B has the following structure:

(B)

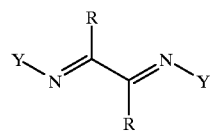

where Y=$SiMe_3$ or H, and R=aryl.

Similar to the compounds disclosed by Buchwald, an article by von Gerdy Tuchtenhagen et al., entitled Darstellung und Reaktionen von 1.2-Bis-trimethylsilyliminen, in *Liebigs Ann. Chem.*, Vol 711, pp. 174–183, (1968), also discloses a compound of formula A, which can be made from a compound of formula B. For the compound of formula A, R=aryl, and E'=S when X=nothing or O, and E'=C($sp^2$) when X=O. For the compound of formula B, Y=$SiMe_3$ or H, and R=aryl. The disadvantage of the compounds of formula B disclosed by Buchwald and Tuchtenhagen, if used as precursors to form other compounds, is that they are not especially reactive because the aryl groups on these molecules only act as weak electron withdrawing groups and because the aryl groups cannot be further functionalized (substituted) readily.

Still further, the Benzildiimine References found in *SciFinder*, Aug. 11, 1998, pp. 1–3, disclose a compound of formula A where R=phenyl, and X=nothing when E'=Se; and X=2 chlorine substituents when E'=Te.

Many of the compounds discussed above are generally unsuited for use in chemical vapor deposition and other processes for several reasons. The disadvantage of some of the compounds of formula A disclosed by Karady, Bertini, Chivers, Roesky, Buchwald, Tuchtenhagen, and SciFinder is that E'=S, Te, Se, all elements that have limited bonding capabilities. It is not as desirable to use these precursors with Group VI elements for chemical vapor deposition because they are only able to bond with 2 compounds, and thus, X must be nothing. In addition, using such compounds to create light emitting diodes is problematic because these compounds do not have substituents that extend the conjugation of the system. Still further, the chemistry of these Group VI elements cannot necessarily be applied to elements that bond with 3 or more elements. Another disadvantage with some of the compounds of formula A disclosed by the articles discussed above, such as that disclosed by Karady, Roesky, Buchwald, Tuchtenhagen, and SciFinder, is that X is Cl or O. The disadvantage with these compounds is that when E' is deposited on a substrate, Cl or O tend to be deposited too. Both of these elements cause contamination of the film being deposited. Still further, when X=Cl, the electronic properties of the compound are altered. Furthermore, Cl and O limit the ability of the compound to further functionalize and therefore are not desirable substituents for enabling these compounds to be used as light emitting diodes. Still further, when X=Cl, the compound is moisture sensitive and decomposes via hydrolysis.

In addition, an article by Manfred Weidenbruch et al., entitled 1,3,2-Diazasiloles by Silylene Addition to Trifluoracetonitrile [1], in *Z. anaorg. allg. Chem.*, Vol 622, pp. 1811–1813, (1996), discloses a compound of formula A where E'=Si, X=2 alkyl substituents, and R=CF$_3$. The method for making this compound involves generation (photochemical) and reaction of a silylene (R$_2$Si:) species, and thus, it is unique to making compounds where E'=Si. Thus, the method disclosed does not suggest how other compounds having E' as another element could be formed.

Several articles by Arthur Ashe and others disclose multistep low yield reactions for producing compounds similar to that of the compound of formula A except that both nitrogens are replaced by carbons, which may have substituents thereon. For these compounds disclosed by Ashe, E'=Sb, As or Bi and R=H or alkyl. These articles are Aromatic Antimony Compounds, Transition Metal Complexes of 2,5-Dimethylstibacyclopentadienyl, by Arthur Ashe et al. in *Journal of Organometallic Chemistry*, Vol. 202, pp. C95–C98, (1980); Synthesis of 2,2',5,5'-Tetramethylbibismole. A Thermochromic Dibismuthine, by Arthur Ashe et al. in *Organometallics*, Vol 3, pp. 495–496, (1984); Synthesis and Molecular and Crystal Structure of 2,2',5,5'-Tetramethylbiarsolyl, by Arthur Ashe et al. in *Organometallics*, Vol. 2, pp. 1005–1008, (1983); and 2,2', 5,5'-Tetramethyldistibolyl. A Thermochromic Distibine, by Arthur Ashe et al. in *Journal of American Chemistry Society*, Vol 103, pp. 207–209, (1981). These articles further disclose that this compound may be used as a thermochromic material.

An article by P. O'Brien et al., entitled Precursor Chemistry: Remaining Challenges and Some Novel Approaches, in *Journal of Crystal Growth*, Vol 170, pp. 23–29 (1997), discloses a compound similar to the compounds disclosed by Arthur Ashe, where both nitrogens in the compound of formula A are replaced by carbons, which may have substituents thereon. This article suggests that these compounds can be used in chemical vapor deposition. The disadvantage with the compounds disclosed by Ashe and O'Brien is that thin films formed using these compounds have carbon contamination because carbon atoms are directly attached to the element E' being deposited on a substrate.

Methods have also been devised for depositing multiple elements on a substrate. The most common approach for chemical vapor deposition of multi-element materials is to use two or more precursors that react individually on the incipient film. The traditional classes of compounds used for the chemical vapor deposition of multi-element thin films involve the reaction of a Group III (B, Al, Ga, In) alkyl with a Group V (N, P, As, Sb, Bi) hydride, alkyl, or alkyl amino compound. One problem with forming these multi-element films with conventional precursors is that the precursors containing the different elements typically differ greatly in their reactivities. This makes it difficult to control the stoichiometry of the film formed. Frequently, the differences in reactivity are countered by using large excesses of the more recalcitrant precursor(s). Still further, these precursors are typically exceedingly pyrophoric and toxic. Thus, when large excesses of a recalcitrant precursor are used, the process creates large amounts of waste that may be toxic.

To overcome the deficiencies found with conventional compounds, a number of novel chemical compounds, methods for making these novel chemical compounds, and applications for using these compounds are needed in the art. More specifically, compounds that may be used as precursors for chemical vapor deposition of thin films are needed. Still further, compounds that can deliver multiple elements in the chemical vapor deposition of thin films are also needed. Still further, compounds that may be used as thermochromic materials, conductive polymers, light-emitting diode precursors, and molecular charge-transfer salt precursors are also needed.

SUMMARY OF THE INVENTION

It is an object of the present invention to provide compounds that can be used as precursors for the chemical vapor deposition of a wide variety of thin films but which lack delivered element-to-carbon bonds so as to reduce carbon contamination in films produced by chemical vapor deposition.

Another object of the present invention is to provide a class of compounds having uniform physical and chemical properties so that there may be greater predictability when producing films or coatings with these compounds.

A further object of the present invention is to provide compounds that may be used as chemical vapor deposition precursors which have two different elements to be delivered therein so as to prevent the waste generated when multiple precursors are used.

It is a farther object of the present invention to provide delivery compounds for elements of Groups II, III, IV, V, and transition elements with greater predictability of the chemical and physical properties of the resultant source compounds so that films and coatings with more uniformity can be produced.

It is a further object of the present invention to provide compounds that have useful optical properties such as being able to change colors upon activation so that these compounds can be used as thermochromic materials.

Another object of the present invention is to provide compounds that have useful electronic properties so that these compounds can be used as precursors for making light-emitting diodes, conductive polymers, or molecular charge-transfer salts.

Still another object of the present invention is to provide molecular charge-transfer salts that have magnetic properties so that they can be used as molecular magnets.

It is another object of the present invention to provide methods of making and using novel compounds that meet the foregoing objects.

According to the present invention, the foregoing and other objects are achieved by novel compounds that may be used as chemical vapor deposition precursors, thermochromic materials, conductive polymers, light-emitting diode precursors, and molecular charge-transfer salt precursors and novel compounds that can be used to make the aforementioned compounds. Still farther, other aspects of the present invention are methods for making and using these compounds.

Additional objects, advantages and novel features of the invention will be set forth in part in the description which follows, and in part will become apparent to those skilled in the art upon examination of the following, or may be learned from practice of the invention. The objects and advantages of the invention may be realized and attained by means of the instrumentalities and combinations particularly pointed out in the appended claims.

DETAILED DESCRIPTION OF THE PREFERRED EMBODIMENT

A butadiene compound of the formula:

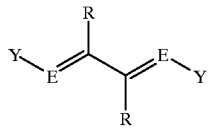
(I)

wherein
  each E is independently selected from the group consisting of N, P, and As;
  each R is independently selected from the group consisting of H, alkyl, aryl, dialkylamino, azide, alkoxy, dipnictaheteroles, polymerizable substituents, and disilylamino; and
  each Y is independently selected from the group consisting of a silyl group and H, is used to make the compounds of the present invention. The silyl group can be Si(trialkyl), Si(triaryl), $SiH_3$, or mixed alkyl/aryl silanes. Preferably, the silyl group is $SiMe_3$. The polynerizable substituent may be, but are not limited to, thiophene, pyrrole, pyridine, aniline, or acetylenic compounds. This compound is a diaza-, diphospha- or diarsabutadiene when E=N, P, or As (the pnictogens), respectively.

Certain butadienes of formula I are novel compounds. Namely, compounds of formula I wherein each E is independently selected from the group consisting of N, P, and As (the pnictogens); each R is independently selected from the group consisting of perfluorinated alkyl, perfluorinated aryl and polymerizable substituents; and each Y is independently selected from the group consisting of a silyl group and H, are novel compounds of the present invention. These novel compounds provide advantages over other butadienes. Specifically, because the perfluorinated compounds have strong electron withdrawing groups thereon, they have better reactivity and, in the instance of chemical vapor deposition, increased volatility. Still further, because the perfluorinated compounds have fluorine substituents, they possess low-lying unoccupied molecular orbitals (LUMOs), which results in them being markedly superior electron acceptors, a characteristic which allows them to function as thermochromic materials, molecular charge-transfer salts, and as electron transporters in light emitting diodes. The compounds with polymerizable substituents can be polymerized to produce electrically conductive polymers. The polymerizable substituents may be thiophene, pyrrole, pyridine, aniline, or acetylenic compounds. Preferably, the polymerizable substituents are 3-thienyl or 3-pyrrolyl because these substituents allow polymerization at the carbon adjacent to the sulfur or nitrogen, respectively, which is desirable.

The butadienes of formula I can be made by three different high yield synthetic pathways. The first approach involves the reaction of an α-dione, which cannot possess enolizable protons, with at least two equivalents of lithium bis(silyl group or hydrogen) amide, to produce the corresponding N,N'-bis(silyl group or hydrogen)-α-diimine. An example of this reaction is shown below:

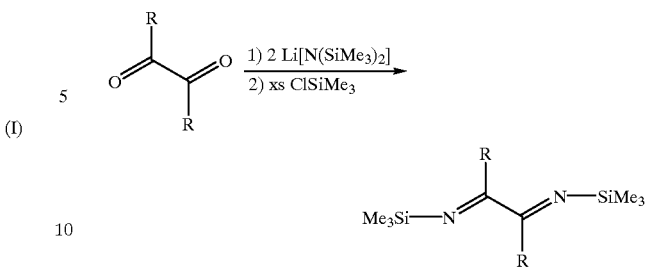

The second approach involves formation of the central carbon-carbon bond of the α-diimie through reductive-coupling of nitrites, as illustrated below:

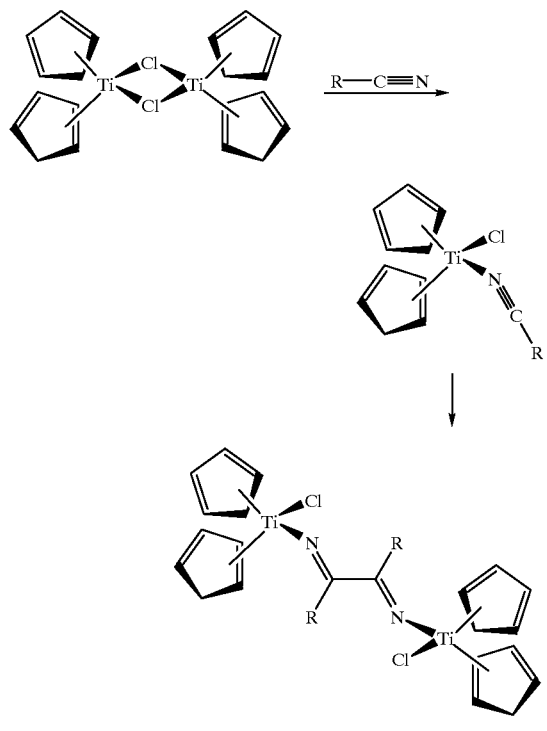

The third synthetic approach is based on the reaction of a photochemically generated silylene, such as $(t\text{-}Bu)_2Si{:}$, with a nitrile such as trifluoroacetonitrile.

The butadiene of formula I is useful for making various novel compounds, namely, compounds of formulas II, III, and IV, discussed infra. It can be reacted with a Lewis acid-base adduct to form a compound of the formula:

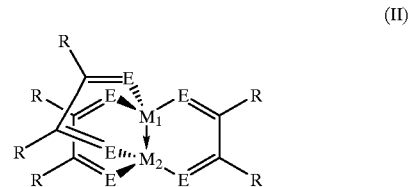
(II)

wherein
  each E is independently selected from the group consisting of N, P, and As;
  each R is independently selected from the group consisting of H, alkyl, aryl, dialkylamino, azide, alkoxy, dipnictaheteroles, polymerizable substituents, and disilylamino;

$M_1$=O, S, Se, Te, Po, N, P, As, Sb, or Bi; and $M_2$ =Be, Mg, Ca, Sr, Ba, Ra, B, Al, Ga, In, or Tl; provided that $M_1$=O, S, Se, Te, or Po when $M_2$=Be, Mg, Ca, Sr, Ba, or Ra, and $M_1$=N, P, As, Sb, or Bi when $M_2$=B, Al, Ga, In, or Tl.

This is another novel compound of the present invention. Preferably, $M_1$ is a Group V element and $M_2$ is a Group III element. Most preferably, each E=N; each R=CF$_3$; $M_1$=P, As, Sb, or Bi; and $M_2$=B, Al, Ga, or In.

Another aspect of the present invention includes reacting a compound of formula I with a Lewis acid-base adduct to form a fused tricyclic compound of formula II. An example of this reaction is shown below:

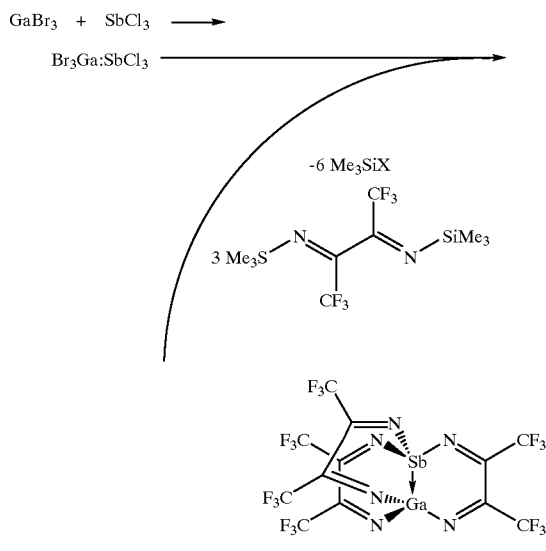

The butadiene of formula I may be reacted with a polyhaloelement so as to form a heterocycle of the formula:

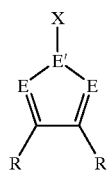

(III)

wherein
each E is independently selected from the group consisting of N, P, and As;

E'=Be, B, C, N, O, Mg, Al, P, Ca, Sc, Ti, V, Cr, Mn, Fe, Co, Ni, Cu, Zn, Ga, Ge, As, Sr, Y, Zr, Nb, Mo, Tc, Ru, Rh, Pd, Ag, Cd, In, Sn, Sb, Ba, La, Hf, Ta, W, Re, Os, Ir, Pt, Au, Hg, Tl, Pb, Bi, Po, Ra, Ce, Pr, Nd, Pm, Sm, Eu, Gd, Tb, Dy, Ho, Er, Tm, Yb, Lu, Th, Pa, U, Np, Pu, Am, Cm, Bk, Cf, Es, Fm, Md, No, or Lr;

X is zero or more substituents independently selected from the group consisting of H, alkyl, aryl, dialkylamino, azide, alkoxy, disilylamino, and dipnictaheteroles, depending upon the valence of E'; and each R is independently selected from the group consisting of H, alkyl, aryl, dialkylamino, azide, alkoxy, dipnictaheteroles, polymerizable substituents, and disilylamino.

The dipnictaheterole of formula III is another compound of the present invention. When each E=N, this compound is a diazaheterozole. E', the element to be delivered, can be a main group element, an alkaline earth metal, a transition element, or a lanthanide element. Preferably, E' is a Group III or Group V element or a transitional metal. Preferably, R is a 6-membered aryl ring having at least one fluorine substituent, $C_1$–$C_3$ dialkylamino having at least one fluorine substituent, $C_1$–$C_3$ alkoxy having at least one fluorine substituent, or $C_1$–$C_3$ alkyl having at least one fluorine substituent.

Another aspect of the present invention is a method of making a compound of formula III. This compound is formed by reacting a polyhaloelement $EZ_nR_p$, where n an integer and p=0 or 1, in a ring-closure reaction, an example of which is shown below:

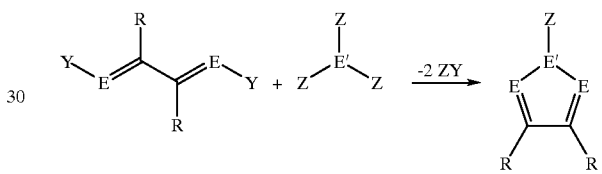

This step is followed by replacing the halogen substituent Z with H, alkyl, aryl, dialkylamino, azide, alkoxy, a dipnictaheterole, a polymerizable substituent, or a disilylamino group, as shown below:

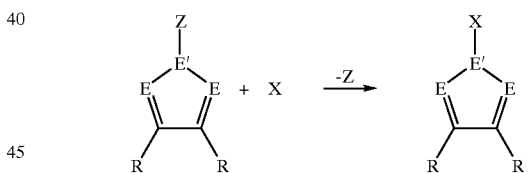

In another embodiment of the present invention, two dipnictaheteroles of formula III can be reacted with each other to form a compound of the formula:

(IV)

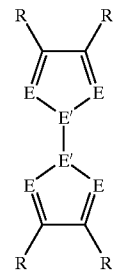

wherein
each E is independently selected from the group consisting of N, P, and As;

each E' is independently selected from the group consisting of Be, B, C, N, O, Mg, Al, Si, P, S, Ca, Sc, Ti, V, Cr, Mn, Fe, Co, Ni, Cu, Zn, Ga, Ge, As, Se, Sr, Y, Zr, Nb, Mo, Tc, Ru, Rh, Pd, Ag, Cd, In, Sn, Sb, Te, Ba, La, Hf, Ta, W, Re, Os, Ir, Pt, Au, Hg, Tl, Pb, Bi, Po, Ra, Ce, Pr, Nd, Pm, Sm, Eu, Gd, Tb, Dy, Ho, Er, Tm, Yb, Lu, Th, Pa, U, Np, Pu, Am, Cm, Bk, Cf, Es, Fm, Md, No, and Lr, provided that the valence of one E' is compatible with the other E' chosen; and each R is independently selected from the group consisting H, alkyl, aryl, dialkylamino, azide, alkoxy, dipnictaheteroles, polymerizable substituents, and disilylamino.

The bi(dipnicta)heterole of formula IV is another novel compound of the present invention. By having two elements for deposition in the same molecule, there is greater predictability in the activity of the molecules. Preferably, one E'=O, S, Se, Te, Po, N, P, As, Sb, or Bi, and the other E'=Be, Mg, Ca, Sr, Ba, Ra, B, Al, Ga, In, or Tl, provided that E'=O, S, Se, Te, or Po when E'=Be, Mg, Ca, Sr, Ba, or Ra, and E'=N, P, As, Sb, or Bi when E'=B, Al, Ga, In, or Tl. Preferably, each R is independently selected from the group consisting of a 6-membered aryl ring having at least one fluorine substituent, $C_1-C_3$ dialkylamino having at least one fluorine substituent, $C_1-C_3$ alkoxy having at least one fluorine substituent, or $C_1-C_3$ alkyl having at least one fluorine substituent.

Another aspect of the present invention is a method of making a compound of formula IV. This compound is formed by reacting two compounds of formula III to form an adduct unit between two heterocycles of formula III. Specifically, this process includes reacting two compounds independently selected from compounds of the formula:

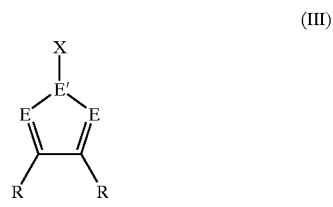

(III)

wherein
each E is independently selected from the group consisting of N, P, and As;

E'=Be, B, C, N, O, Mg, Al, Si, P, S, Ca, Sc, Ti, V, Cr, Mn, Fe, Co, Ni, Cu, Zn, Ga, Ge, As, Se, Sr, Y, Zr, Nb, Mo, Tc, Ru, Rh, Pd, Ag, Cd, In, Sn, Sb, Te, Ba, La, Hf, Ta, W, Re, Os, Ir, Pt, Au, Hg, Tl, Pb, Bi, Po, Ra, Ce, Pr, Nd, Pm, Sm, Eu, Gd, Tb, Dy, Ho, Er, Tm, Yb, Lu, Th, Pa, U, Np, Pu, Am, Cm, Bk, Cf, Es, Fm, Md, No, or Lr;

X=H, alkyl, aryl, dialkylamino, azide, alkoxy, halogen, or dipnictaheteroles; and each R is independently selected from the group consisting of H, alkyl, aryl, dialkylamino, azide, alkoxy, dipnictaheteroles, polymerizable substituents, and disilylamino.

This reaction can be a condensation reaction performed in the presence of a silyl group. An example of this reaction is shown below:

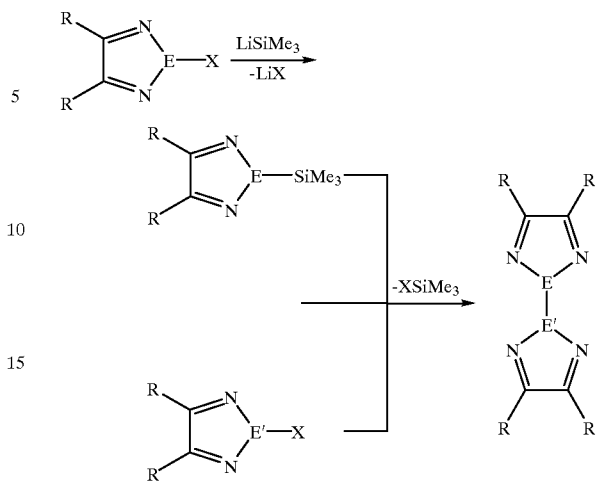

Alternatively, the reaction can involve the metallation of a dipnictaheterole of formula m with Li, Na, or Mg so as to form a heterocyclopentadienide ion, followed by reacting the ion with a compound of formula III via a MX-elimination reaction. An example of this reaction is shown below, and n is usually 1 or 2:

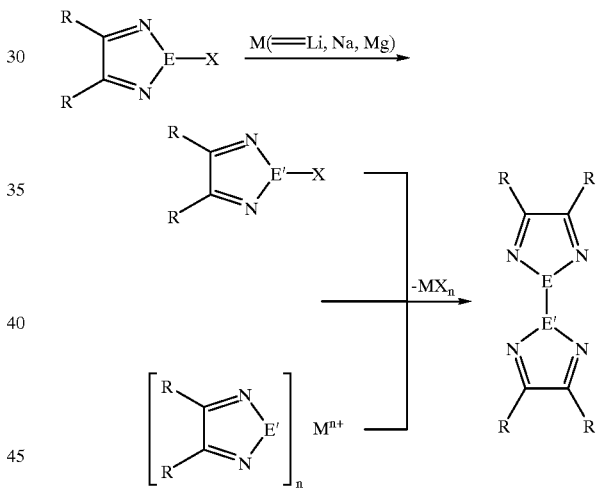

The compounds of formulas II, III, and IV are useful for chemical vapor deposition (CVD). More specifically, these compounds may be used as source compounds or precursors for the chemical vapor deposition of thin films, such as epitaxial layers, passivation layers, diffusion layers, hard and/or decorative coatings, corrosion protective coatings, optical coatings, whisker crystals, fibers and bulk single crystals. This application is another embodiment of the present invention and involves depositing one or more elements on a substrate by transporting a compound of formula II, III, or IV over the substrate and depositing one or more elements E', which are a part of the compound, on the substrate. E' may be separated from the compound by decomposing the compound by subjecting it to heat. The possible substrates include flat surfaces, filaments, and powders. The substrate should have a good lattice match with the film being deposited.

For chemical vapor deposition, a precursor carried in a carrier gas is passed over a hot surface. This action initiates a chemical reaction in which one of the products is a thin film of a solid, such as a metal, semi-conductor, or insulator, depending upon what elements are deposited. Most CVD reactions require rather high temperatures, often over 1000° C. However, using the methods of the present invention, the compounds can be decomposed at temperatures between about 150 and 800° C. In many cases, the compounds can be decomposed at temperatures below about 400° C. Still further, the process of the present invention allows for the recovery and recycle of starting materials so as to prevent pollution.

Using the CVD precursors of the present invention offers the opportunity to achieve greater uniformity in reactivity for each precursor. Specifically, heterocycles of formula II, III, or IV containing different elements E', the delivered atom, incorporated into their ring-structures bearing the same ring-substituents would likely exhibit very similar physical and chemical characteristics with regard to both volatility and reactivity. Still further, compounds of formulas II and IV provide single source precursors with uniform, predictable reactivity at both "ends" (two E' within the same compound) of the precursor, thus allowing multiple elements to be deposited with a single precursor. The volatile molecular precursors of the present invention allow the vapor-phase transport in deposition of high quality films of Group III-V (tuneable band-gap) semi-conductors, Group III-nitride films, metal nitrides, and metal phosphides.

A compound of formula III, where each E is independently selected from N, P, or As; E' is Si or $C(sp^2)$; X represents at least one substituent wherein each substituent is independently selected from the group consisting of alkyl, aryl, dialkylamino, and alkoxy provided that X represents one substituent when $E'=C(sp^2)$ and two substituents when E'=Si; and each R is independently selected from the group consisting of H, alkyl, aryl, dialkylamino, azide, alkoxy, dipnictaheteroles, a polymerizable substituent, and disilylamino, is also useful as a light emitting diode. This application is a further embodiment of the present invention. A light emitting diode is a multi-layer device. A light emitting diode is made by placing a transparent anode on a glass substrate. Next, an electron donor layer is placed on the transparent anode. Following this, an electron transporting layer is placed on the electron donor layer. Then, a cathode is placed on the electron transporting layer. The electron transporting layer is comprised of a compound of formula III, as described above, dispersed within a polymeric film. This may be done by dissolving the compound of formula III in the polymer or by covalently attaching it to the polymer backbone. Preferably, the transparent anode is an indium tin oxide (ITO) anode. Preferably, the electron donor layer is comprised of poly(p-phenylenevinylene) (PPV). Preferably, the cathode is a metal with a low work function, such as aluminum. When a voltage is applied between the cathode and the anode, a light emitting diode is formed, and light is emitted through the glass substrate.

Compound IV is also useful as an electrically conductive polymer, a thermochromic material, and a molecular charge-transfer salt. These applications are all further embodiments of the present invention.

In order to form electrically conductive polymers, compound IV is polymerized to form the compound shown below:

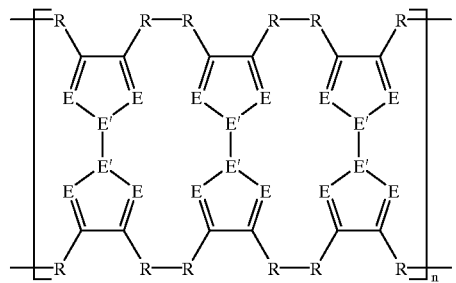

wherein
each E is independently selected from the group consisting of N, P, and As;
each E' is independently selected from the group consisting of As, Sb, and Bi or both $E'=C(sp^2)$ or both E' together represent a single Pt;
each R is a polymerizable substituent; and
n=any integer.

The polymerizable substituent can be polymerized either chemically or electrochemically. When both $E'=C(sp^2)$, a double bond is formed between E' and E', and such a structure is preferable. Each R may be independently selected from thiophene, pyrrole, pyridine, aniline, or acetylenic compounds. Preferably, poly(thiophene) or poly (pyrrole) form the ladder "uprights" linked by bi(dipnicta) heteroles or tetrapnictafulvalenes as the "rungs" of the ladder. The "uprights" of the ladder are the conductive part of the molecule. This electrically conductive polymer is a further embodiment of the present invention.

In order to form a thermochromic material, a compound of formula IV is selected, where each E is independently selected from the group consisting of N, P, and As; each E' is independently selected from the group consisting of As, Sb, Bi, and P; and each R is independently selected from H, alkyl, aryl, dialkylamino, azide, alkoxy, dipnictaheteroles, polymerizable substituents, or disilylamino. Then, this compound is crystallized. This is a further embodiment of the present invention. The thermochromic materials change colors upon activation, such as by exposure to heat.

In order to form a molecular charge-transfer salt, a compound of formula IV, where $E'=C(sp^2)$ and a double bond is formed between E' and E', is selected. When E=N, compound IV is an electron acceptor, and when E=P or As, compound IV is an electron donor. One example of how a compound of formula IV, where E=N, is formed is shown below:

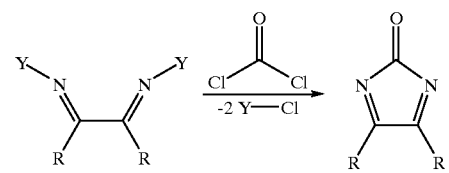

Y = silyl group or H

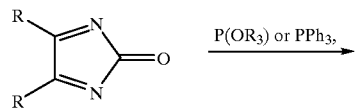

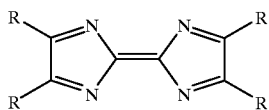

An alternative way to form a compound of formula IV when E=N is shown below:

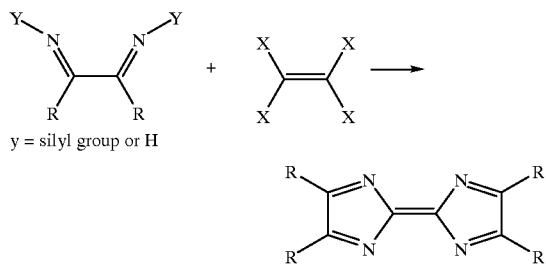

y = silyl group or H

When E=N, this compound is mixed with an electron donor, such as tetrathiafuilvalene (TTF) or a compound of formula IV where E=P or As. When E=P or As, this compound is mixed with an electron acceptor, such as tetracyanoethylene (TCNE), tetracyanoquinodimethane (TCNQ), or a compound of formula IV where E=N. The electron donor and the electron acceptor are combined in a ratio of between about 2:1 and 1:2 to form a mixture. Next, the mixture is co-crystallized. The donors and acceptors are stacked in a segregated stacking architecture where there is intermolecular electronic orbital overlap between adjacent donors and adjacent acceptors. The compound of formula IV must be a substantially planar molecule so that it may be stacked. Still further, the donor undergoes partial oxidation and the acceptor undergoes partial reduction. These partial charge-transfers can happen naturally during the co-crystallization of the mixture, or the transfers can be induced chemically or electrochemically. In some cases, these molecular charge-transfer salts can be molecular magnets. In other cases, these salts can function as light emitting diodes. These molecular charge-transfer salts are a further embodiment of the present invention.

The following are examples of the novel compounds of the present invention and methods of making these compounds. Because many of the reagents employed and/or products derived from the synthesis described below are air and/or moisture sensitive, all reactions and manipulations were carried out under inert atmosphere [glove box and double manifold (Schlenk) line] using anhydrous and air-free solvents and reagents. These examples are presented for illustrative purposes only and are not in any way intended to limit the scope of the present invention. It is further contemplated that alternative synthesis methods may be used by those of ordinary skill in the art to manufacture the compounds of the present invention.

EXAMPLE 1
METHOD FOR MAKING A DIAZABUTADIENE, NAMELY, N,N'-BIS(TRIMETHYLSILYL)-1,2-BIS (TRIFLUOROMETHYL)ETHANEDIIMINE

A quantity of 80.0 gm (412.3 mmol) of perfluorobiacetyl (PFBA; 1,1,1,4,4,4-hexafluor-2,3-butanedione), $F_3CC(O)C(O)CF_3$, was dissolved in approximately 500 mL of an anhydrous solvent, preferably a non-polar hydrocarbon solvent, and maintained at between −78° C. and 0° C. (PFBA boils at 20° C.) in a reaction flask with attached stopcock and a vented addition funnel. In the vented addition funnel was 142.25 gm (824.6 mmol) $LiN[Si(CH_3)_3]_2$ dissolved in approximately 300 mL anhydrous solvent, again preferably a non-polar hydrocarbon solvent. To the cold PFBA solution, the lithium amide solution was added dropwise with stirring. After the addition was complete, the reaction mixture was allowed to warm slowly to room temperature; the reaction mixture was then stirred at room temperature for 16–20 hours. The reaction mixture was then refluxed for 6–8 hours, and then cooled back to room temperature. To the homogeneous reaction mixture was added, via syringe, approximately 115 mL (900 mmol) $ClSi(CH_3)_3$. The reaction mixture was then stirred for approximately 12–20 hours at room temperature, during which time a large quantity of LiCl was observed to precipitate from solution. The reaction mixture was then heated to and stirred at approximately 60° C. for approximately 6–8 hours. The reaction mixture was then cooled to room temperature and filtered through Celite® (or other suitable filter aid) on a coarse fritted funnel. The hexane was then removed, via atmospheric pressure distillation, and then the remaining product mixture was vacuum distilled at 25–26° C./400–450 mtorr to yield 86.7 g (63%) of N2N'-bis(trimethyls2yl)-bis (trifluoromethyl)ethanediimine, $(CH_3)_3Si$—N=C($CF_3$)—($CF_3$)C=N—Si($CH_3$)$_3$. Elemental analysis was carried out: calcd (found) for $C_{10}H_{18}N_2F_6Si_2$: C, 35.7%(35.83%), H, 5.39% (5.42%), N, 8.33% (8.29%), F, 33.88% (33.78%), Si 16.70% (16.85%). $^{13}C[^1H]NMR$ ($\delta$; $CD_2Cl_2$)155.4 ppm (>C=N—, q, $J^2$=36.33 Hz), 116.9 ppm (—$CF_3$, q, $J^1$=286.7 Hz), 1.4 ppm [—Si($CH_3$)$_3$, s]. Infrared $v_{C=N}$=1714, 1716 $cm^{-1}$. Mass spectral analysis results (EI, 70 eV) [m/e (species, relative abundance %)]: 336 ($M^+$, 0.25), 168 ($M^+$/2, 23.10), 73 [—Si($CH_3$)$_3$, 100].

EXAMPLE 2
METHOD FOR MAKING A DIAZABUTADIENE, NAMELY, N,N'-BIS(TRIMETHYLSILYL)-1,2-BIS (PENTAFLUOROPHENYL)ETHANEDIIMINE

To a suspension of 15.5 g (39.7 mmol) of decafluorobenzil, $C_6F_5C(O)C(O)C_6F_5$, in approximately 500 mL of anhydrous cyclohexane was added dropwise, at approximately 5°–10° C., 15.9 g (92.3 mmol) of lithium bis(trimethylsilyl)amide, $LiN[Si(CH_3)_3]_2$. After the addition was complete, the reaction was refluxed for approximately 6–8 hours. The reaction was then cooled to approximately 5°–10° C. and approximately 13 mL (100 mmol) $ClSi(CH_3)_3$ was added slowly via syringe. The reaction was then stirred for 16–20 hours at room temperature, followed by 5–8 hours at 50°–70° C. The dark red solution was cooled to room temperature and filtered through a fritted funnel with Celite® (or other suitable filter aid) to remove lithium chloride, and the solvent was removed in vacuo. The residue was re-dissolved in approximately 200 mL of hot (40°–60° C.) anhydrous hexane, and then cooled to dry ice temperature (approximately −70° to −80° C.). Approximately 5 gm (9.5 mmol, 24%) of crystalline product, N,N'-bis (trimethylsilyl)-1,2-bis(pentafluorophenyl)ethanediimine, was separated by filtration of the cold suspension through a fritted funnel. $^{13}C$ NMR ($\delta$; $CD_2Cl_2$) 158.3 ppm (>C=N—, s), 143.5 (dm, $J^1$=244.4 Hz), 141.6 dm, $J^1$=253.3 Hz), 137.6 (dm, $J^1$=253.7 Hz), 114.8 ppm (ipso C, t, $J^2$=22.85 Hz), −1.1 ppm [—Si($CH_3$)$_3$]. Infrared ($C_6H_6$)$v_{C=N}$=1684.6, 1696 $cm^{-1}$. Elemental analysis was cared out: calcd (found) for $C_{20}H_{18}N_2F_{10}Si_2$: C, 45.11% (45.33%), H, 3.41% (3.52%), N, 5.26% (5.19%), F, 35.68% (35.55%), Si 10.55% (10.35%).

EXAMPLE 3
METHOD FOR MAKING A DIAZABUTADIENE, NAMELY, N,N'-BIS(TRIMETHYLSILYL)-1,2-BIS(3-THIENYL)ETHANEDIIMINE

To a solution of 15.0 g (67.5 mmol) of Di-3-thienylglyoxal (3,3'-dithenyl), $C_4H_3SC(O)C(O)C_4H_3S$, in approximately 300 mL of anhydrous methylcyclohexane was added dropwise, at approximately −75° C. (dry ice/isopropyl alcohol bath), 22.58 g (135 mmol) of lithium bis(trimethylsilyl)amide, $LiN[Si(CH_3)_3]_2$ dissolved in approximately 250 mL anhydrous methylcyclohexane. After the addition was complete, the reaction was allowed to warm to room temperature, and stirred at room temperature for approximately 16–20 hours. Next, the reaction mixture was heated to 60°–70° C. for approximately 6–8 hours. The reaction was then cooled to approximately 0° C., and approximately 20 mL (158 mmol) $ClSi(CH_3)_3$ was added slowly via syringe. The reaction was then stirred for 16–20 hours at room temperature, followed by 5–8 hours at 50°–70° C. The dark red-orange solution was cooled to room temperature and filtered through a fritted funnel with Celiteg (or other suitable filter aid) to remove lithium chloride, and the solvent was removed in vacuo. The residue was re-dissolved in approximately 200 mL of hot (40°–60° C.) anhydrous hexane, and then cooled to dry ice temperature (approximately −70° to −80° C.). Approximately 17.7 gm (48.6 mmol, 72%) of the orange crystaine product N,N-'bis(trimethylsilyl)-1,2-bis(3-thienyl)ethanediimine, was separated by filtration of the cold suspension through a fritted funnel. $^{13}C$ NNR ($\delta$; $CD_2Cl_2$) 166.7 ppm (>C=N—), 136.4, 132.2, 127.6, 126.3 ppm, −1.1 ppm [—$Si(CH_3)_3$]. Infrared ($C_6H_6$): $\nu_{C=N}$=1664.6, 1646 $cm^{-1}$. Elemental analysis was carried out: calcd (found) for $C_{16}H_{24}N_2S_2Si_2$: C, 52.70% (52.63%), H, 6.63% (6.52%), N, 7.68% (7.59%), S, 17.59% (17.54%), Si 15.40% (15.35%).

EXAMPLE 4
METHOD FOR MAKING A DIAZABUTADIENE, NAMELY, 1,1,1,4,4,4-HEXAFLUORO-2,3-BUTANEDIIMINE

In the glove box, 64.1 g (150 mmol) of $[(\eta^5—C_5H_5)_2TiCl]_2$ was weighed into a two-necked 1.0 L reaction flask w/stopcock. The flask was brought out of the glove box, attached to the Schienk line, and approximately 500 mL of anhydrous toluene added via cannula. The flask was freeze-thaw degassed and 30.88 g (325 mmol) trifluoroacetonitrile, $CF_3CN$, condensed into the flask at liquid nitrogen temperature (−196° C.). The reaction mixture was allowed to warm to approximately −78° C. (dry ice/isopropanol bath), and stirred at this temperature for approximately 4–8 hours, after which time it was allowed to warm to room temperature. After stirring at room temperature for approximately 12–20 hours, the mixture was filtered, and the bright yellow precipitate washed with anhydrous pentane until the washings were clear and colorless. The yellow microcrystalline solid was dried in vacuo to yield 87.9 g (95%) of [$\mu$-[1,1,4,4,4-hexafluoro-2,3-butanediimniato(2-)-N:N']]tetrakis($\eta^5$-2,4-cyclopentadien-1-yl)dichlorodititanium.

In a 1.0 L two-necked reaction flask with stopcock, fitted with an overhead stirrer and vented addition funnel, 150.0 g (243 mmol) of [$\mu$-[1,1,4,4,4-hexafluoro-2,3-butanediiminato(2-)-N:N']]tetrakis($\eta^5$-2,4-cyclopentadien-1-yl)dichlorodititaniurn was suspended in approximately 500 mL anhydrous diethyl ether. Ethereal HCl (HCl/diethyl ether, 1.0 M, 5 10 mL/510 mmol) was added to the vented addition funnel. The reaction mixture was cooled to approximately −78° C. (dry ice/isopropanol bath), and the ethereal HCl was added dropwise over approximately 1 hour. The reaction mixture was allowed to warm slowly to approximately 0° C. (ice/water bath), and the mixture stirred at this temperature for an additional 1–3 hours. Upon completion of reaction, the volatile components were vacuum transferred into a separate 1.0 L flask, leaving behind ($\eta^5$—$C_5H_5$)$_2$TiCl$_2$, which can be recycled back to [($\eta^5$—$C_5H_5$)$_2$TiCl]$_2$ (overall yield 70–75%)for re-use. The volatile components are then atmospherically distilled to yield first, the solvent (ether), and then the product 1,1,1,4,4,4-hexafluoro-2,3-butanediimine, H—N=C(CF$_3$)—(CF$_3$)C=N—H [35.5 g, 185 mmol (76%)]; b.p.=80–81° C., m.p.=52.9° C.]. Elemental analysis was carried out: calcd (found) for $C_4H_2N_2F_6$: C, 25.01% (25.03%), H, 1.05% (1.12%), N, 14.59% (14.53%), F, 59.35% (59.28%). $^{13}C[^1H]$NMR ($\delta$; $CD_2Cl_2$) 158.7 ppm (>C=N—; q, $J^2$=33.47 Hz), 117.6 ppm (—CF$_3$, q, $J^1$=282.1 Hz). $^1H$ NMR ($\delta$; $CD_2Cl_2$) 12.07 ppm (—NH). Infrared $\nu_{C=N}$=1718 $cm^{-1}$.

EXAMPLE 5
METHOD FOR MAKING A DIAZABUTADIENE, NAMELY, 1,2-DI(PENTAFLUOROPHENYL)-ETHANEDIIMINE

In the glove box, 21.35 g (50 mmol) of [($\eta^5$—$C_5H_5$)$_2$TiCl]$_2$ was weighed into a two-necked 500 mL reaction flask w/stopcock. The flask was brought out of the glove box, attached to the Schlenk line, and approximately 200 mL of anhydrous toluene added via cannula. The reaction mixture was cooled to approximately −78° C. (dry ice/isopropanol bath), and 13.6 mL (21.3 g, 110 mmol) pentafluorobenzonitrile was added dropwise, via syringe. The reaction mixture was stirred at this temperature for approximately 4–8 hours, after which time it was allowed to warm to room temperature. After stirring at room temperature for approximately 12–20 hours, the mixture was filtered, and the red-orange precipitate washed with anhydrous pentane until the washings were clear and colorless. The red-orange solid was dried in vacuo to yield 30.5 g (75%) of tetrakis($\eta^5$-2,4-cyclopentadien-1-yl)[$\mu$[1,2-di(pentafluorophenyl)ethanediiminato(2-)-N:N']dichlorodititaniurn.

In a 500 mL two-necked reaction flask with stopcock, fitted with an overhead stirrer and vented addition funnel, 50.0 g (61.5 mmol) of tetrakis($\mu^5$-2,4-cyclopentadien-1-yl)[$\mu$-[1,2-di(pentafluorophenyl)ethanediiminato(2-)-N:N'] dichlorodititanium was suspended in approximately 200 mL anhydrous diethyl ether. Ethereal HCl (HCl/diethyl ether, 1.0 M, 130 mL/130 mmol) was added to the vented addition funnel. The reaction mixture was cooled to approximately −78° C. (dry ice/isopropanol bath), and the ethereal HCl was added dropwise over approximately 1 hour. The reaction mixture was allowed to warm slowly to approximately 0° C. (ice/water bath), and the mixture stirred at this temperature for an additional 1–3 hours. Upon completion of reaction, the reaction mixture was filtered through a fritted funnel and the precipitate [($\eta^5$—$C_5H_5$)$_2$TiCl$_2$]was washed with 2×50 mL ether. The solvent was removed in vacuo, and the residue was re-dissolved in approximately 100 mL anhydrous $CH_2Cl_2$, and filtered again to remove insoluble materials. The $CH_2Cl_2$ solution was cooled overnight at approximately −70° to −80° C. (dry ice/isopropanol), and then filtered cold to yield the orange crystalline product 1,2-di (pentafluorophenyl)-ethanediimine, H—N=C($C_6F_5$)—($C_6F_5$)C=N—H[15.5 g, 40 mmol (65%)]. Elemental analysis was carried out: calcd (found) for $C_4H_2N_2F_6$: C, 43.32% (43.43%), H, 0.52% (0.61%), N, 7.22% (7.32%) (48.91%). $^{13}C[^1H]$NMR ($\delta$; $CD_2Cl_2$) 158.2 ppm (>C=N—; t, $J^3$13.3 Hz), 112.4 ppm (i, t, $J^2$=23.6 Hz), 138.4 ppm (dt, $J^1$=253.3 Hz), 142.7 (dm, $J^1$=254.1 Hz), 144.5 ppm (dd, $J^1$=248.9 Hz). $^1H$ NMR ($\delta$; $CD_2Cl_2$) 12.42 ppm (—NH). Infrared $\nu_{C=N}$=1657 $cm^{-1}$.

EXAMPLE 6
A METHOD FOR MAKING A DIAZAHETEROLE, NAMELY, 2-CHLORO-4,5-DI(TRIFLUOROMETHYL)-1,3,2-DIAZASTIBOLE

In the glove box, a 1.0 L two-necked reaction flask with stopcock was charged with 50.5 g (150 mmol) of N,N'-bis(trimethylsilyl)-1,2-bis(trifluoromethyl)ethanediimine, $(CH_3)_3Si-N=C(CF_3)-(CF_3)C=N-Si(CH_3)_3$, which was made in Example 1. A solids addition tube, containing 34.22 g (150 mmol) of $SbCl_3$ was attached to the flask and the flask was removed from the glove-box. Approximately 600 mL of anhydrous benzene was added via cannula, and the solution cooled to approximately 5°–10° C. (benzene freezes at 6° C.); the $SbCl_3$ was added slowly via the solids addition tube. The reaction mixture was stirred at room temperature overnight, followed by approximately 6–10 hours at approximately 60°–70° C. The reaction mixture was then cooled to room temperature and filtered through a fritted funnel. The orange microcrystalline product was then washed first with 2×50 mL anhydrous $CH_2Cl_2$, followed by 2×50 mL anhydrous pentane, and then dried in vacuo. The product, 2-chloro-4,5-di(trifluoromethyl)-1,3,2-diazastibole was obtained in approximately 95% yield (49.5 g, 143 mmol). For purification, the product can either be sublimed (95° C., 50 mtorr), or recrystallized from, e.g., anhydrous tetrahydrofuran, from which it crystallizes as a 1:1 solvate. $^{13}C[^1H]NMR$ ($\delta$; $CD_2Cl_2$) 155.6 ppm (>C=N—; q, $J^3$=34.8 Hz), 123.85 ppm (—$CF_3$, t, $J^1$=280.5 Hz). Elemental analysis was carried out: calcd (found) for $C_4N_2ClF_6Sb$: C, 13.84% (13.73%), N, 8.07% (8.01%), Cl 10.21% (10.38%), F, 32.83% (32.76%), Sb 35.06% (35.22%).

EXAMPLE 7
METHOD FOR MAKING A DIAZAHETEROLE, NAMELY, 2-CHLORO-4,5-DI(TRIFLUOROMETHYL)-1,3,2-DIAZABISMOLE

In the glove box, a 500 mL two-necked reaction flask with stopcock was charged with 16.8 g (50 mmol) of N,N'-bis(trimethylsilyl)-1,2-bis(trifluoromethyl)ethanediimine, $(CH_3)_3Si-N=C(CF_3)-(CF_3)C=N-Si(CH_3)_3$, which was made in Example 1. A solids addition tube, containing 15.77 g (50 mmol) of $BiCl_3$ was attached to the flask and the flask was removed from the glove-box. Approximately 300 mL of anhydrous benzene was added via cannula, and the solution cooled to approximately 5°–10° C. (benzene freezes at 6° C.); the $BiCl_3$ was added slowly via the solids addition tube. The reaction mixture was stirred at room temperature overnight, followed by approximately 6–10 hours at approximately 60°–70° C. The reaction mixture was then cooled to room temperature and filtered through a fritted funnel. The red-orange microcrystalline product was then washed first with 2×50 mL anhydrous $CH_2Cl_2$, followed by 2×50 mL anhydrous pentane, and then dried in vacuo. The product, 2-chloro-4,5-di(trifluoromethyl)-1,3,2-diazabismole was obtained in approximately 92% yield (19.99 g, 46 mmol). Elemental analysis was carried out: calcd (found) for $C_4N_2ClF_6Bi$: C, 11.06% (10.91%), N, 6.45% (6.32%), Cl 8.16% (8.38%), F, 26.24% (26.06%), Bi 48.10% (48.32%).

EXAMPLE 8
A METHOD FOR MAKING A DIAZAHETEROLE, NAMELY, BIS[p-[$\mu$-[1,1,1,4,4,4-BUTANEDIIMINATO(2-)-N:N,N']DIBROMODIGALLIUM

A solution of 15.47 g (50 mmol) of $GaBr_3$ dissolved in approximately 300 mL of anhydrous hexane was added slowly (over approximately 30–60 min), at approximately 0° C., to a solution of 16.8 g (50 mmol) of diimine. This diimine was N,N'-bis(trimethylsilyl)-1,2-bis(trifluoromethyl)ethanediine, which was made in Example 1. A light yellow microcrystalline product formed and deposited immediately from the reaction solution. The mixture was stirred for an additional 2–4 hr at 0° C., and then at room temperature for approximately 1–2 hours. The mixture was filtered through a fritted funnel, and the solids washed with 2×50 mL cold anhydrous pentane. The product can be recrystallized from cold $CH_2Cl_2$ to yield 20.94 g (85%, 42.5 mmol) of bis[$\mu$[N-trimethylsilyl)-1,1,1,4,4,4-butanediiminato(2-)-N:N,N']tetrabromodigallium, which exists in solution and in the solid state as a dimer. Elemental analysis was carried out: calcd (found) for $C_{14}H_{18}N_4Br_4F_{12}Ga_2Si_2$ (dimeric unit): C, 17.06% (17.17%), H, 1.84% (2.00%), N, 5.68% (5.86%), Br, 32.43% (32.38%), F, 23.13% (22.86%), Ga 14.15% (14.29%), Si, 14.15% (14.02%).

The product, bis[$\mu$[N-trimethylsilyl)-1,1,1,4,4,4-butanediiminato(2-)-N:N,N']tetrabromodigallium, was the result of elimination of only one equivalent of $BrSi(CH_3)_3$. Elimination (dehalosilylation) of the second equivalent of $BrSi(CH_3)_3$ can be accomplished by heating the bis[$\mu$[N-trimethylsilyl)-1,1,1,4,4,4-butanediiminato(2-)-N:N,N'] tetrabromodigallium compound in a hydrocarbon solvent at 60°–110° C. for 4–12 hours. For example, 10.0 g (10.2 mmol, as the dimeric unit) of bis[$\mu$[N-trimethylsilyl)-1,1,1,4,4,4-butanediiminato(2-)-N:N,N']tetrabromodigallium was refluxed for approximately 6–8 hr in anhydrous octane. The reaction mixture was then cooled to room temperature and filtered through a medium porosity flitted funnel, and the solvent was removed from the filtrate in vacuo. The filtrate was then dissolved in approximately 100 mL $CH_2Cl_2$, filtered through a flitted funnel with Celiteg (or other suitable filter aid), and the solvent was removed in vacuo. The product, bis[$\mu$[N-trimethylsilyl)-1,1,1,4,4,4butanediiminato(2-)-N:N,N']dibromodigallium, was obtained. The light yellow microcrystalline product was obtained in 65% yield (2.25 g, 6.6 mmol). Elemental analysis was carried out: calcd (found) for $C_8N_4Br_2F_{12}Ga_2$ (dimeric unit): C, 14.14% (14.27%), N, 8.25% (8.36%), Br, 23.52% (23.68%), F, 33.56% (33.41%), Ga 20.53% (20.71%).

EXAMPLE 9
A METHOD FOR MAKING A DIAZAHETEROLE, NAMELY, 2-PHENYL-4,5-DI(2,2,2-TRIFLUOROETHOXY)-1,3,2-DIAZASTIBOLE

The compound 1,2-di(2,2,2-trifluoroethoxy)ethanediimine (1.2 g, 5 mmol) was placed into a 50 mL Schlenk flask and the flask was flushed with nitrogen. Approximately 20 mL anhydrous diethyl ether was added, and the solution was cooled to approximately −70° to −80° C. (dry ice/isopropanol). Ten mmol (4.9 mL, 2.03M) n-butyllithium/hexane was then added dropwise via syringe; the solution was stirred at −78° C. for approximately 30 minutes. A solution of 1.35 g (5.0 mmol) of phenylantimony dichloride [$(C_6H_5)SbCl_2$] in 25 mL of ether was then added dropwise via syringe. The reaction mixture was allowed to warm to room temperature while stirring. After stirring at room temperature for approximately 1–2 hours, the mixture was filtered through a fritted funnel, and the filtrate evaporated in vacuo. The solid residue was sublimed (1 torr, room temperature) to yield the white crystalline product 2-phenyl-4,5-di(2,2,2-trifluoroethoxy)-1,3,2-diazastibole in 45% yield (1.01 g, 2.25 mmol). $^{13}C[^1H]NMR$ ($\delta$; $CD_2Cl_2$) 156.0 ppm (>C=N—; s), 152.2, 132.2, 131.5, and 129.3 ppm (phenyl C), 124.8 ppm (—$CF_3$, t, $J^1$=278.0 Hz), 63.7 ppm (q, $J^2$=34.9Hz). Elemental analysis was carried out: calcd (found) for $C_{12}H_9N_2O_2F_6Sb$: C, 32.10% (32.17%), H, 2.02% (2.09%), N, 6.24% (6.31%), F, 25.39% (25.43%), Sb 27.12% (27.20%).

EXAMPLE 10
A METHOD FOR MAKING A DIAZAHETEROLE, NAMELY, 2-CHLORO-4,5-[9,10,c]-PHENANTHRO-1,3,2-DIAZASTIBOLE

A benzene solution (~200 mL) of lithium bis(trimethylsilyl)amide (340mmol), was added via a vented addition funnel to 35.40 g (170 mmol) of 9,10-phenanthrenedione suspended in 200 mL of benzene. After addition of the amide solution was complete, the temperature of the now homogeneous solution was maintained at 6° C. for 1 hr, after which the temperature was allowed to slowly warm to 20° C. After 4 hr, the solution color had changed from an initial dark green to a deep red. With stirring, the solution was warmed to 70° C. for 20 hr. After 20 hr, the solution was cooled to 20° C., and 50 mL (390 mmol) of chlorotrimethylsilane was added via syringe to the stirring solution. Stirring was continued at 60° C. for another 5 hr. The solution was then cooled to room temperature and filtered through a medium porosity Schlenk frit with Celite® (or other suitable filter aid), to remove lithium chloride, and the solvent was removed in vacuo. The filtrate was redissolved in 250 mL of toluene to which 75 mL of pentane was also added. The solution was cooled to −78° C. for 24 hr. The orange crystalline product was obtained by filtration through a coarse Schlenk frit, and subsequently washed with cold pentane (−78° C.). A yield of 53.50 g (90%) of phenanthrenequinone-(9,10)-bis(trimethylsilyl)diimine was obtained, mp=148° C. Anal. calcd (found) for $C_{20}H_{26}N_2Si_2$: C, 68.51% (68.73%), H, 7.47% (7.52%), N, 7.99% (7.91%). $^1$H NMR (δ; $CD_2Cl_2$) 7.6–6.6 ppm (multiplet, 8H), 0.2 ppm (s, 18H); $^{13}C[^1H]$NMR (δ; $CD_2Cl_2$) 171.1 ppm (>C=N—), 135.1, 131.8, 128.1, 127.9 123.8 ppm (phenanthro C), 1.4 ppm [—Si(CH$_3$)$_3$]. Infrared (KBr pellet) $v_{C=N}$=1663, 1643 cm$^{-1}$. MS (EI, 15 eV) [m/e (relative abundance %)]: 350 (M$^+$, 12.4), 238 (21.9), 237 (100), 207 (24.1), 206 (35.8), 73 (—SiMe$_3$, 68.3), 45 (18.7).

In the glove box: (i) 3.50 g (10 mmol) of the diimine prepared above was placed into a 100 mL Schlenk flask equipped with a magnetic stirring bar and a septum; and (ii) 2.28 g (10 mmol) of SbCl$_3$ was placed in a solids-addition tube. Freshly distilled benzene (55 mL) was added to the flask containing the diimine; under a flow of nitrogen the solids-addition tube was joined to the flask. With stirring, the antimony trichloride was added slowly to the orange diimine solution. The reaction mixture was stirred for 24 hr at room temperature and was subsequently filtered through a medium-porosity Schlenk frit. The precipitate was washed with 20–30 mL of benzene and dried in vacuo. The yield of the orange-brown solid, 2-Chloro-4,5-[9,10,c]-phenanthro-1,3,2-diazastibole (mp 223° C., dec.) was 3.54 g (98%). Anal. calcd (found) for $C_{14}H_8N_2ClSb$: C, 46.52% (46.10%), H, 2.23% (2.14%), N, 7.75% (7.58%), Cl, 9.81% (9.97%), Sb, 33.69% (33.81%).

EXAMPLE 11
A METHOD FOR MAKING A DIAZAHETEROLE, NAMELY, 2-CHLORO-4,5-DIPHENYL-1,3,2-DIAZASTIBOLE

A benzene solution (~200 mL) of lithium bis(trimethylsilyl)amide (340 mmol), was added via a vented addition funnel to 35.73 g (170 mmol) of benzil dissolved in 200 mL of benzene. After addition of the amide solution was complete, the temperature of the solution was maintained at 6° C. for 1 hr, after which the temperature was allowed to slowly warm to 20° C. Stirring of the deep red solution was continued for 3 hr at 20° C., then for 7 hr at 70° C. The solution was cooled to 20° C., and 50 mL (390 mmol) of chlorotrimethylsilane was added via syringe to the stirring solution. Stirring was continued at 60° C. for another 5 hr. The yellow solution was cooled to 20° C. and filtered through a medium-porosity Schlenk frit with Celite® (or other suitable filter aid) to remove lithium chloride and the solvent was removed in vacuo. The filtrate was vacuum distilled (bp=150° C., 1 torr), and yielded 57 gm (96%) of yellow crystalline N,N'-bis(trimethylsilyl)-1,2-diphenyl-ethanediimine (mp=69–70° C.). Anal. calcd (found) for $C_{20}H_{28}N_2Si_2$: C, 68.12% (68.52%), H, 8.00% (8.04%), N, 7.94% (7.86%) (δ; $CD_2Cl_2$) 174.7 ppm (>C=N—), 138.7, 131.6, 128.8, 128.6 ppm (phenyl C), 0.5 ppm [—Si(CH$_3$)$_3$]. Infrared (KBr pellet) $v_{C=N}$=1661, 1644cm$^{-1}$.

In the glove box: (i) 3.50 g (10 mmol) of the diimine prepared above was placed into a 100 mL Schlenk flask equipped with a magnetic stirring bar and a septum; and (ii) 2.28 g (10 mmol) of SbCl$_3$ was placed in a solids-addition tube. Freshly distilled benzene (55 mL) was added to the flask containing the diimine; under a flow of nitrogen the solids-addition tube was joined to the flask. With stirring, the antimony trichloride was added slowly to the yellow diimine solution. The reaction mixture was stirred for 24 hr at room temperature and was subsequently filtered through a medium-porosity Schlenk frit. The precipitate was washed with 20–30 mL of benzene and dried in vacuo. The yield of the orange solid, 2-chloro-4,5-diphenyl- 1,3,2-diazastibole 84%. Anal. calcd (found) for $C_{14}H_{10}N_2ClSb$: C, 46.27% (46.11%), H, 2.77% (2.64%), N, 7.71% (7.60%), Cl, 9.75% (9.91%), Sb, 33.50% (33.61%). CP-MAS $^{13}$C NMR (δ; 75.432 MHz) 172.8 ppm (>C=N—), 138.7, 136.7, 135.1, 127.9 ppm (phenyl C).

EXAMPLE 12
A METHOD FOR MAKING A DIAZAHETEROLE, NAMELY, 2-CHLORO-4,5-[9,10,c]-PHENANTHRO-1,3,2-DIAZABISMOLE

In the glove box: (i) 3.50 g (10 mmol) of the diimine, phenanthrenequinone-(9,10)-bis(trimethylsilyl)diimine, was placed into a 100 mL Schlenk flask equipped with a magnetic stirring bar and a septum; and (ii) 3.15 g (10 mmol) of BiCl$_3$ was placed in a solids-addition tube. The preparation of this diimine is shown in Example 10. Freshly distilled benzene (55 mL) was added to the flask containing the diimine; under a flow of nitrogen the solids-addition tube was joined to the flask. With stirring, the bismuth trichloride was added slowly to the orange diiinine solution. After addition of the solid, a reflux condenser was attached to the flask, and the reaction mixture was refluxed for 24 hr. After refluxing, the solution was cooled and was subsequently filtered through a medium-porosity Schlenk frit. The precipitate was washed with 30 mL of THF, followed by 20 mL of pentane, and dried in vacuo to yield (orange-brown solid, mp 204–208° C., dec.) 4.13 g (92%) of 2-Chloro-4,5-[9,10,c]-phenanthro-1,3,2-diazabismole. Anal. calcd (found) for $C_{14}H_8N_2ClBi$: C, 37.48% (37.41%), H, 1.80% (1.84%), N, 6.24% (6.28%), Cl, 7.90% (8.09%), Bi, 46.58% (46.81%).

EXAMPLE 13
A METHOD FOR MAKING A CHARGE-TRANSFER PRECURSOR, NAMELY, PHENANTHRENEQUINONEIMIDAZOLONE

In the glove box, 46.3 g (132.0 mmol) of diimine, phenanthrenequinone-(9,10)-bis(trimethylsilyl)diimine, was weighed into a 1.0 L reaction flask with stopcock. The preparation of this diimine is shown in Example 10. The flask was removed from the glove box and attached to the vacuum line. Approximately 500 mL of anhydrous toluene was added via cannula, and the mixture was freeze-thaw degassed three times. The reaction mixture was cooled to approximately −70° to −80° C. (dry ice/isopropanol bath), and 13.13 g (132.7 mmol) of phosgene ($Cl_2C=O$) was condensed into the flask. The flask was sealed and the contents allowed to warm to 0° C. (ice/water bath). The reaction was stirred at 0C for approximately 2–6 hours, and then allowed to warm to and stir at room temperature overnight. The product, obtained as a red solid, was isolated by filtration on a fritted funnel, and washed with 2×75 mL anhydrous hexane, and dried in vacuo. The yield of 4,5-[9,10,c]-phenanthro-2H-imidazol-2-one was 97% (29.74 g, 128 mmol). This product may also be referred to as phenanthrenequinoneimidazolone. $^{13}C[^1H]NMR$ (δ; $CDCl_3$) 179.0 ppm (>C=O—; s), 152.9 ppm (>C=N—; s), 137.6, 137.0, 135.8, 131.1, 130.0, 128.3, and 125.0 (phenanthro Cs). Elemental analysis was carried out: calcd (found) for $C_{15}H_8N_2O$: C, 77.58% (77.67%), H, 3.47% (3.52%), N, 12.06% (12.01%), O, 6.89% (6.82%).

EXAMPLE 14
A METHOD FOR MAKING A CHARGE-TRANSFER PRECURSOR, NAMELY, DECAFLUOROBENZILIMIDAZOLONE

Analogous to Example 13, 5.33 g (10 mmol) of N,N'-bis(trimethylsilyl)-1,2-di(pentafluorophenyl)-ethanediimine, which was made in Example 2, was reacted with 10 mmol (1.0 g) of phosgene to yield 3.4 g (8.2 mmol, 82%) of 4,5-di(pentafluorophenyl)-2H-imidazol-2-one as a dark red solid. This product is also referred to as decafluorobenzilimidazolone. $^3C[^1H]NMR$ (δ; $CDCl_3$) 177.6 ppm (>C=O—; s), 156.2 ppm (>C=N—; t, $J^3$=13.4 Hz), 112.6 ppm (i, t, $J^2$=23.6 Hz), 138.1 ppm (dt, $J^1$=254 Hz), 142.7 (dm, $J^1$=254 Hz), 144.5 ppm (dd, $J^1$=249 Hz). Elemental analysis was carried out: calcd (found) for $C_{15}F_{10}N_2O$: C, 43.50% (43.57%), F, 45.87% (45.82%), N, 6.76% (6.71%), O, 3.86% (3.78%).

EXAMPLE 15
A METHOD FOR MAKING A DIAZAHETEROLE, NAMELY, 2-[BIS(2,2,2-TRIFLUOROETHYL)]AMIDO-4,5-DI(TRIFLUOROMETHYL)]1,3,2-DIAZASTIBOLE

To a slurry of 17.36 g (50 mmol) of 2-chloro-4,5-di(trifluoromethyl)-1,3,2-diazastibole, which was prepared in Example 6, in approximately 300 mL anhydrous ether, maintained at approximately −70° to −80° C. (dry ice/isopropanol bath), a freshly prepared solution of 50 mmol $Li[N(CH_2CF_3)_2]$ in approximately 100 mL anhydrous hexane was added dropwise over 30–60 minutes. The reaction mixture was then allowed to warm to room temperature, and then stirred at room temperature overnight. The solvent was removed in vacuo, and the residue was sublimed (50° C., 200 mtorr) to yield 20.9 g (42.5 mmol, 85%) of 2-[bis(2,2,2-trifluoroethyl)]amido-4,5-di(trifluoromethyl)-1,3,2-diazastibole. Elemental analysis was carried out: calcd (found) for $C_8H_4N_3F_{12}Sb$: C, 19.53% (19.41%), H, 0.82% (0.8%), N, 8.54% (8.42%), F, 46.35% (46.21%), Sb 24.75% (24.85%). $^{13}C[^1H]NMR$ (δ; $CD_2Cl_2$) 157.9 ppm (>C=N—; q, $J^2$=35.9 Hz), 126.9 ppm (—$CF_3$, q, $J^1$=282.1 Hz), 123.6 ppm (—$CF_3$, q, $J^1$=281.8 Hz), 53.05 ppm (—$CH_2$—, q, $J^2$=31.77 Hz). $^1H$ NMR (δ; $CD_2Cl_2$) 3.57 ppm (—$CH_2$—, q, $J^3$=9.40 Hz).

EXAMPLE 16
A METHOD FOR MAKING A DIAZAHETEROLE, NAMELY, 2-BIS(TRIMETHYLSILYL)AMIDO-4,5-[9,10,C]-PHENANTHRO-1,3,2-DIAZASTIBOLE

In the glove box: (i) 1.81 g (5 mmol) of 2-chloro-4,5-[9,10,c]-phenanthro-1,3,2-diazabismole, which was prepared in Example 10, was placed in a 100 mL Schlenk flask equipped with a magnetic stir bar and a septum; and (ii) 0.84 g (5 mmol) of $Li[N(SiMe_3)_2]$ was placed in a 50 mL Schlenk flask containing a magnetic stir bar and fitted with a septum. To each flask was added 35 mL of freshly distilled benzene. After the $Li[N(SiMe_3)_2]$ was completely dissolved in benzene, both flasks were cooled to 6° C. and, with the use of a cannula, a slow dropwise addition (1 drop/sec) of the amide to the stirred slurry of 2-chloro-4,5-[9,10,c]-phenanthro-1,3,2-diazabismole was initiated. Upon completion of the addition, the reaction mixture was slowly warmed to 20° C. and stirring was continued for an additional 24 hr. The solution was then filtered through a medium-porosity Schlenk frit with Celite® (or other suitable filter aid) to remove lithium chloride. The filtrate was dried in vacuo, and the solid was recrystallized from $CH_2Cl_2$ to yield 2.06 g (85%) of the deep red crystalline solid 2-bis(trimethylsilyl)amido-4,5-[9,10,c]-phenanthro-1,3,2-diazastibole (mp 124–125° C., dec.). $^{13}C$ NMR ($CD_2Cl_2$): δ169.0 (>$\underline{C}$=N—), δ134.6,134.4, 132.4, 128.7, 123.7 (phenanthro C), δ5.2 [-Si($\underline{C}H_3$)$_3$]. Anal. calcd (found) for $C_{20}H_{26}N_3Si_2Sb$ C, 49.39% (49.52%), H, 5.39% (5.44%), N, 8.64% (8.72%), Sb, 25.03% (25.04%).

EXAMPLE 17
A METHOD FOR MAKING A DIAZAHETEROLE, NAMELY, 2-BIS(TRIMETHYLSILYL)AMIDO-4,5-DIPHENYL-1,3,2-DIAZASTIBOLE

The analogous compound 2-bis(trimethylsilyl)amido-4,5-diphenyl-1,3,2-diazastibole (orange solid) was prepared and isolated in a manner identical to the process of Example 16, in 70% yield (mp 120° C., dec.). However, 2-chloro-4,5-diphenyl-1,3,2-diazastibole, which was prepared in Example 11, was used as the starting material in place of 2-chloro-4,5-[9,10,c]-phenanthro-1,3,2-diazastibole. Anal. calcd (found) for $C_{20}H_{28}N_3Si_2Sb$:C, 49.19% (49.31%), H, 5.78% (5.84%), N, 8.60% (8.65%), Sb, 24.93% (24.91%). $^{13}C$ NMR ($CD_2Cl_2$): δ176.0 (>$\underline{C}$=N—), δ142.2, 129.4, 128.8, 127.9 (phenyl C), 35.8 [—Si($\underline{C}H_3$)$_3$].

EXAMPLE 18
A METHOD FOR MAKING A DIAZAHETEROLE, NAMELY, 2-BIS(TRIMETHYLSILYL)AMIDO-4,5-DIPHENYL-1,3,2-DIAZABISMOLE

The analogous 2-bis(trimethylsilyl)amido-4,5-diphenyl-1,3,2-diazabismole (dark red solid) was prepared and isolated in a manner identical to the processes of Examples 16 and 17, in 85% yield (mp 130°–135° C., dec.). However, 2-chloro-4,5-[9,10,c]-phenanthro-1,3,2-diazabismole, which was prepared in Example 12, was used as a starting material. Anal. calcd (found) for $C_{20}H_{26}N_3Si_2Bi$:C, 41.88% (41.72%), H, 4.57% (4.44%), N, 7.33% (7.42%), Bi, 36.43% (36.31%). $^{13}C$ NMR ($CD_2Cl_2$: δ174.6 (>$\underline{C}$=N—), δ149.5, 135.8, 131.9, 128.2, 126.9, 124.2 (phenanthro C), δ5.7 [—Si($\underline{C}H_3$)$_3$].

EXAMPLE 19
A METHOD OF MAKING A FUSED-RING TRICYCLIC III-V SINGLE-SOURCE PRECURSOR

A fused-ring tricyclic III-V single-source precursor containing Ga and Sb in a 1:1 ratio is prepared. $GaBr_3$ and $SbBr3$ are mixed to form a Lewis acid-base adduct $Br_3Ga:SbBr_3$, followed by reaction of the adduct with more than three equivalents of the diimine N,N'-bis(trimethylsilyl)-1,2-bis(trifluoromethyl)ethanediimine, which is prepared according to Example 1, in a suitable anhydrous, non-polar hydrocarbon solvent, at a temperature between 60 and 80° C. This temperature is suitable to effect a dehalosilylation/ring-closure reaction. The fused-ring tricyclic single-source precursor is purified by vacuum distillation.

EXAMPLE 20
A METHOD OF MAKING A FUSED-RING TRICYCLIC III-V SINGLE-SOURCE PRECURSOR

A fused-ring tricyclic III-V single-source precursor containing Ga and Sb in a 1:1 ratio is prepared. $GaBr_3$ and $SbBr_3$ are mixed to form a Lewis acid-base adduct $Br3Ga:SbBr_3$. Next, the diimine 1,1,1,4,4,4-hexafluoro-2,3-butanediimine, which is prepared according to Example 4, is deprotonated at between −70 and −80° C. with s-butyllithium, a strong base. Three equivalents of the deprotonated diimine are reacted with one equivalent of the Lewis acid:base adduct ($Br_3Ga:SbBr3$) at room temperature to effect a metal salt-elimination reaction. The fused-ring tricyclic single-source precursor is purified by vacuum distillation.

EXAMPLE 21
A METHOD OF MAKING A FUSED-RING TRICYCLIC III-V SINGLE-SOURCE PRECURSOR

A fused-ring tricyclic III-V single-source precursor containing Ga and Sb in a 1:1 ratio is prepared. $GaBr_3$ and $SbBr_3$ are mixed to form a Lewis acid-base adduct $Br_3Ga:SbBr_3$. Next, three equivalents of the diimine 1,1,1,4,4,4-hexafluoro-2,3-butanediimine, which is prepared according to Example 4, is reacted with triethylamine, a hydrogen halide-scavenging base. This product is then reacted with the adduct in a 3:1 ratio. This reaction is performed in an anhydrous non-polar hydrocarbon solvent at elevated temperatures suitable to effect the HCl-elimination/ring-closure reaction. The fused-ring tricyclic single-source precursor is purified by vacuum distillation.

EXAMPLE 22
A METHOD OF MAKING A BICYCLIC SINGLE-SOURCE PRECURSOR

A Group V diazaheterole is reacted with $LiSiMe_3$ to produce 2-trimethylsilyl-1,3,2-diazaheterole. This diazaheterole is subsequently condensed with a Group III 2-halo 1,3,2-diazaheterole via a $ClSiMe_3$-elimination reaction.

EXAMPLE 23
A METHOD OF MAKING A BICYCLIC SINGLE-SOURCE PRECURSOR

The metallation of a Group V 2-phenyl-diazaheterole is performed with Na. 1,3,2-diazaheterocyclopentadienide ion is formed. After the metallation, the ion is reacted with a Group III 2-halo-1,3,2-diazaheterole via a MX-elimination reaction.

EXAMPLE 24
A METHOD OF MAKING A MOLECULAR CHARGE-TRANSFER SALT

Two equivalents of an imidazolone, namely, decafluorobenzilimidazolone, which is prepared according to Example 16, are coupled with triphenyl phosphine, a trivalent phosphorus compound. An electron acceptor is formed. The product is purified by chromatography. The compound is then mixed with the electron donor tetrathiafulvalene (TTF). Next, the mixture is co-crystallized so as to form a molecular charge-transfer salt.

EXAMPLE 25
A METHOD OF MAKING A MOLECULAR CHARGE-TRANSFER SALT

The diimine N,N'-bis(trimethylsilyl)-1,2-bis(trifluoromethyl)ethanediimine, which is made according to Example 1, is reacted with thiophosgene. This product is coupled with itself with the use of trimethyl phosphite, a trivalent phosphorus compound. An electron acceptor is formed. The product is purified by sublimation. The compound is then mixed with the electron donor tetrathiafulvalene (TTF). Next, the mixture is electrocrystallized so as to form a molecular charge-transfer salt.

EXAMPLE 26
A METHOD OF MAKING A THERMOCHROMIC MATERIAL

A thermochromic material is prepared by coupling two equivalents of a diazaheterole, namely, 2-chloro-4,5-di(trifluoromethyl)-1,3,2-diazastibole, which is prepared according to Example 6. These diazaheteroles are reductively coupled via metallation with magnesium metal. The product is purified by sublimation. Following this, the product is crystallized.

EXAMPLE 27
A METHOD OF MAKING A THERMOCHROMIC MATERIAL

A thermochromic materials is prepared by coupling two equivalents of a diazaheterole, namely, 2-phenyl-4,5-[9,10,c]-phenanthro-1,3,2-diazabismole, which are prepared according to a method similar to that of Example 10. These diazaheteroles are reductively metallated with sodium, followed by the oxidative coupling of the diazabismacyclopentadienides using iodine. The product is purified by recrystallization. Following this, the product is crystallized.

EXAMPLE 28
A METHOD OF MAKING A THERMOCHROMIC MATERIAL

A thermochromic material is prepared by coupling two diazaheteroles. This coupling is accomplished by the dehalosilylation of a 2-trimethylsilyl-1,3,2-diazaheterole with the corresponding 2-chloro-1,3,2-diazaheterole. The product is purified by recrystallization. Following this, the product is crystallized.

EXAMPLE 29
A METHOD OF MAKING AN ELECTRICALLY CONDUCTIVE POLYMERS

N,N'-bis(trimethylsilyl)-1,2-bis(3-thienyl)ethanediimine, which is prepared according to Example 3, is reacted with $AsCl_3$ to form a 2-chloro-4,5-di(3-thienyl)-1,3,2-diazaarsole. This diazaheterole is reductively coupled to form a thermochromic bicyclic diazaheterole with appended thiophene rings. This monomer is electropolymerized to produce a ladder-conjugated polymer where the poly(thiophene) forms the conductively ladder uprights, and the bi(dipnicta)heteroles, which are stacked in a direction perpendicular to the poly(thiophene) chains, form the ladder rungs.

EXAMPLE 30
A METHOD OF MAKING AN ELECTRICALLY CONDUCTIVE POLYMERS

N,N'-bis(trimethylsilyl)-1,2-bis(pyrrole)ethanediimine, which is prepared according to Example 3, is reacted with SbCl₃ to form a 2-chloro-4,5-di(pyrrole)-1,3,2-diazaheterole. This diazaheterole is reductively coupled to form a thermochromic bicyclic diazaheterole with appended thiophene rings. This monomer is electropolymerized to produce a ladder-conjugated polymer where the poly(pyrrole) forms the conductively ladder uprights, and the bi(dipnicta)heteroles, which are stacked in a direction perpendicular to the poly(pyrrole) chains, form the ladder rungs.

EXAMPLE 31
A METHOD OF MAKING AN ELECTRICALLY CONDUCTIVE POLYMERS

N,N'-bis(trimethylsilyl)-1,2-bis(3-thienyl)ethanediimine, which is prepared according to Example 3, is reacted with phosgene to form a corresponding imidazolone, namely 4,5-di(3-thienyl)-2H-imidazol-2-one. This imidazolone is coupled with triphenyl phosphite to form a tetrapnictafulvalene with appended thiophene rings. This monomer is electropolymerized to produce a ladder polymer where the poly(thiophene) forms the electrically conductive ladder uprights, and the tetrapnictafulvalene compounds, which are stacked in a direction perpendicular to the poly(thiophene) chains, form the ladder rungs.

EXAMPLE 32
A METHOD OF MAKING AN ELECTRICALLY CONDUCTIVE POLYMERS

N,N'-bis(trimethylsilyl)-1,2-bis(3-thienyl)ethanediimine, which is prepared according to Example 3, is reacted with thiophosgene to form a corresponding imidazolthione, namely, 4,5-di(3-thienyl)-2H-imidazol-2-thione. This imidazolthione is coupled with trimethyl phosphite to form a tetrapnictafulvalene with appended thiophene rings. This monomer is electropolymerized to produce a ladder polymers where the poly(thiophene) forms the electrically conductive ladder uprights, and the tetrapnictafulvalene compounds, which are stacked in a direction perpendicular to the poly(thiophene) chains, form the ladder rungs.

From the foregoing, it will be seen that this invention is one well adapted to attain all the ends and objects hereinabove set forth together with other advantages which are obvious and inherent to the compounds, methods, and uses disclosed. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

I claim:

1. A compound of the formula:

wherein
each E is independently selected from the group consisting of N, P, and As;
each R is independently selected from the group consisting of perfluorinated alkyl, perfluorinated aryl, and polymerizable substituents; and
each Y is independently selected from the group consisting of a silyl group and H.

2. The compound of claim 1, wherein R=CF₃ and Y=SiMe₃.

3. A compound of the formula:

wherein
each E is independently selected from the group consisting of N, P, and As;
each R is independently selected from the group consisting of H, alkyl, aryl, dialkylamino, azide, alkoxy, dipnictaheteroles, polymerizable substituents, and disilylamino;
$M_1$=O, S, Se, Te, Po, N, P, As, Sb, or Bi; and
$M_2$=Be, Mg, Ca, Sr, Ba, Ra, B, Al, Ga, In, or Tl;

provided that
$M_1$=O, S, Se, Te, or Po when $M_2$=Be, Mg, Ca, Sr, Ba, or Ra, and
$M_1$=N, P, As, Sb, or Bi when $M_2$=B, Al, Ga, In, or Tl.

4. The compound of claim 3, wherein $M_1$=P, As, Sb, or Bi, and $M_2$=B, Al, Ga, or In.

5. The compound of claim 4, wherein R=CF₃.

6. A compound of the formula:

wherein
each E is independently selected from the group consisting of N, P, and As;
E'=Be, B, C, N, O, Mg, Al, P, Ca, Sc, Ti, V, Cr, Mn, Fe, Co, Ni, Cu, Zn, Ga, Ge, As, Sr, Y, Zr, Nb, Mo, Tc, Ru, Rh, Pd, Ag, Cd, In, Sn, Sb, Ba, La, Hf, Ta, W, Re, Os, Ir, Pt, Au, Hg, Tl, Pb, Bi, Po, Ra, Ce, Pr, Nd, Pm, Sm, Eu, Gd, Tb, Dy, Ho, Er, Tm, Yb, Lu, Th, Pa, U, Np, Pu, Am, Cm, Bk, Cf, Es, Fm, Md, No, or Lr;
X is zero or more substituents independently selected from the group consisting of H, alkyl, aryl, dialkylamino, azide, alkoxy, disilylamino, and dipnictaheteroles, depending upon the valence of E'; and
each R is independently selected from the group consisting of H, alkyl, aryl, dialkylamino, azide, alkoxy, dipnictaheteroles, polymerizable substituents, and disilylamino.

7. The compound of claim 6, wherein each R is independently selected from the group consisting of a 6-membered aryl ring having at least one fluorine substituent, $C_1$–$C_3$ dialkylamino having at least one fluorine substituent, $C_1$–$C_3$ alkoxy having at least one fluorine substituent, and $C_1$–$C_3$ alkyl having at least one fluorine substituent.

8. A compound of the formula:

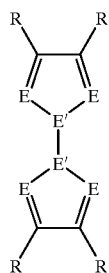

wherein
each E is independently selected from the group consisting of N, P, and As;
each E' is independently selected from the group consisting of Be, B, C, N, O, Mg, Al, Si, P, S, Ca, Sc, Ti, V, Cr, Mn, Fe, Co, Ni, Cu, Zn, Ga, Ge, As, Se, Sr, Y, Zr, Nb, Mo, Tc, Ru, Rh, Pd, Ag, Cd, In, Sn, Sb, Te, Ba, La, Hf, Ta, W, Re, Os, Ir, Pt, Au, Hg, Tl, Pb, Bi, Po, Ra, Ce, Pr, Nd, Pm, Sm, Eu, Gd, Th, Dy, Ho, Er, Tm, Yb, Lu, Th, Pa, U, Np, Pu, Am, Cm, Bk, Cf, Es, Fm, Md, No, and Lr, provided that the valence of one E' is compatible to form a bond with the other E' chosen; and
each R is independently selected from the group consisting H, alkyl, aryl, dialkylamino, azide, alkoxy, dipnictaheteroles, polymerizable substituents, and disilylamino.

9. The compound of claim 8, wherein one E'=O, S, Se, Te, Po, N, P, As, Sb, or Bi, and the other E'=Be, Mg, Ca, Sr, Ba, Ra, B, Al, Ga, In, or Tl, provided that one E'=O, S, Se, Te, or Po when the other E'=Be, Mg, Ca, Sr, Ba, or Ra, and one E'=N, P, As, Sb, or Bi when the other E'=B, Al, Ga, In, or Tl.

10. The compound of claim 9, wherein each R is independently selected from the group consisting of a 6-membered aryl ring having at least one fluorine substituent, $C_1$–$C_3$ dialkylamino having at least one fluorine substituent, $C_1$–$C_3$ alkoxy having at least one fluorine substituent, and $C_1$–$C_3$ alkyl having at least one fluorine substituent.

11. A method for making a fused tricyclic compound of the formula:

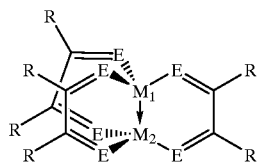

wheremn
each E is independently selected from the group consisting of N, P, and As;
each R is independently selected from the group consisting of H, alkyl, aryl, dialkylamnino, azide, alkoxy, dipnictaheteroles, and disiyamino;
$M_1$=O, S, Se, Te, Po, P, As, Sb, or Bi; and
$M_2$=Be, Mg, Ca, Sr, Ba, Ra, B, Al, Ga, or In,
provided that
M=O, S, Se, Te, or Po when $M_2$=Be, Mg, Ca, Sr, Ba, or Ra, and
$M_1$=N, P, As, Sb, or Bi when $M_2$=B, Al, Ga, In, or Tl,
comprising:

forming a Lewis acid-base adduct; and
reacting said adduct with at least three compounds of the formula:

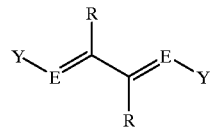

wherein
each E is independently selected from the group consisting of N, P, and As;
each R is independently selected from the group consisting of H, alkyl, aryl, dialkylamino, azide, alkoxy, dipnictaheteroles, polymerizable substituents, and disilylarnino; and
each Y is independently selected from the group consisting of a silyl group and H.

12. A method for making a compound of the formula:

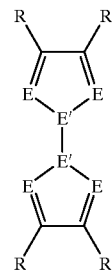

wherein
each E is independently selected from the group consisting of N, P, and As;
each E' is independently selected from the group consisting of Be, B, C, N, O, Mg, Al, Si, P, S, Ca, Sc, Ti, V, Cr, Mn, Fe, Co, Ni, Cu, Zn, Ga, Ge, As, Se, Sr, Y, Zr, Nb, Mo, Tc, Ru, Rh, Pd, Ag, Cd, In, Sn, Sb, Te, Ba, La, Hf, Ta, W, Re, Os, Ir, Pt, Au, Hg, Tl, Pb, Bi, Po, Ra, Ce, Pr, Nd, Pm, Sm, Eu, Gd, Tb, Dy, Ho, Er, Tm, Yb, Lu, Th, Pa, U, Np, Pu, Am, Cm, Bk, Cf, Es, Fm, Md, No, and Lr provided that the valence of one E' is compatible to form a bond with the other E' chosen; and
each R is independently selected from the group consisting H, alkyl, aryl, dialkylamino, azide, alkoxy, perfluoroalkyl, polyfluoroalkoxy, dipnictaheteroles, polymerizable substituents, and disilylamino,
comprising:
reacting two compounds independently selected from compounds of the formula:

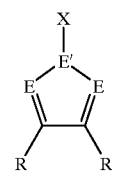

wherein
each E is independently selected from the group consisting of N, P, and As;
E'=Be, B, C, N, O, Mg, Al, Si, P, S, Ca, Sc, Ti, V, Cr, Mn, Fe, Co, Ni, Cu, Zn, Ga, Ge, As, Se, Sr, Y, Zr, Nb, Mo, Tc, Ru, Rh, Pd, Ag, Cd, In, Sn, Sb, Te, Ba, La, Hf, Ta, W, Re, Os, Ir, Pt, Au, Hg, Tl, Pb, Bi, Po, Ra, Ce, Pr, Nd, Pm, Sm, Eu, Gd, Th, Dy, Ho, Er, Tm, Yb, Lu, Th, Pa, U, Np, Pu, Am, Cm, Bk, Cf, Es, Fm, Md, No, or Lr;

X is zero or more substituents independently selected from the group consisting of H, alkyl, aryl, dialkylamino, azide, alkoxy, and disilylamnino, depending upon the valence of E'; and each R is independently selected from the group consisting of H, alkyl, aryl, dialkylamino, azide, alkoxy, dipnictaheteroles, a polymerizable substituent, and disilylamino.

13. The method of claim 12, wherein said reaction is a condensation reaction performed in the presence of a silyl group.

14. The method of claim 12, wherein said reaction is comprised of the metallation of a dipnictaheterole of formula III with Li, Na, or Mg so as to form a heterocyclopentadienide ion, followed by reacting said ion with a compound of formula III via a Mx-elimination reaction.

15. A method for depositing an element on a substrate, comprising:

transporting a compound selected from the group consisting of compounds of formula (II), (III), and (IV), as shown below:

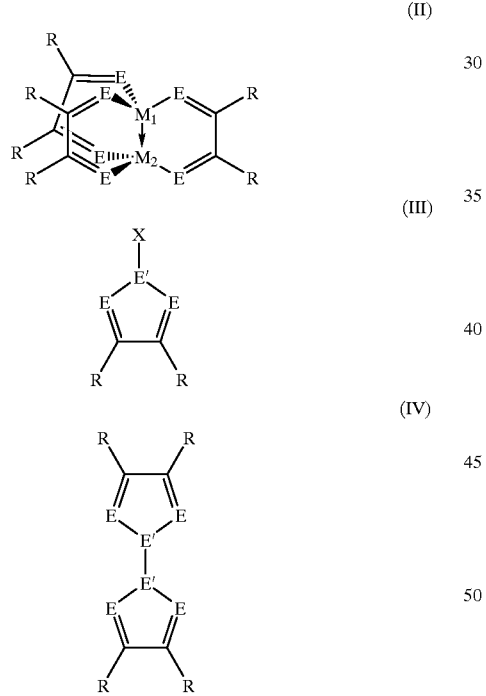

wherein each E is independently selected from the group consisting of N, P, and As;

E'=Be, B, C, N, O, Mg, Al, Si, P, S, Ca, Sc, Ti, V, Cr, Mn, Fe, Co, Ni, Cu, Zn, Ga, Ge, As, Se, Sr, Y, Zr, Nb, Mo, Tc, Ru, Rh, Pd, Ag, Cd, In, Sn, Sb, Te, Ba, La, Hf, Ta, W, Re, Os, Ir, Pt, Au, Hg, Tl, Pb, Bi, Po, Ra, Ce, Pr, Nd, Pm, Sm, Eu, Gd, Th, Dy, Ho, Er, Tm, Yb, Lu, Th, Pa, U, Np, Pu, Am, Cm, Bk, Cf; Es, Fm, Md, No, and Lr;

X=H, alkyl, aryl, dialkylamino, azide, alkoxy, or diazaheterozole;

each R is independently selected from the group consisting of H, alkyl, aryl, dialkylamino, azide, alkoxy, perfluoroalkyl, polyfluoroalkoxy, diazaheterozole, and disilylamino; and $M_1$=O, S, Se, Te, Po, N, P, As, Sb, or Bi;

$M_2$=Be, Mg, Ca, Sr, Ba, Ra, B, Al, Ga, In, or Tl; and provided that $M_1$=O, S, Se, Te, or Po when $M_2$=Be, Mg, Ca, Sr, Ba, or Ra, and $M_1$=N, P, As, Sb, or Bi when $M_2$=B, Al, Ga, In, or Tl, over said substrate; and decomposing said compound so as to release an element E' on said substrate.

16. The method of claim 15, wherein said compound is decomposed at a temperature between about 150 and 800° C.

17. The method of claim 15, wherein said compound is decomposed at a temperature below about 400° C.

18. A method for making an electrically conductive polymer, comprising:

polymerizing monomers of the formula:

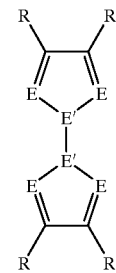

wherein each E is independently selected from the group consisting of N, P, and As;

each E' is independently selected from the group consisting of As, Sb, and Bi or both E'=C(sp²) or both E' together represent a single Pt; and each R is a polymerizable substituent, so as to form a compound of the formula:

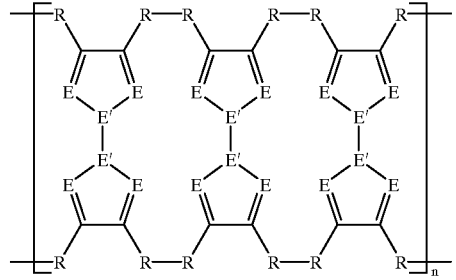

wherein

E and E' are defined above;

R is a monomeric unit of a polymer; and n=any integer.

19. The electrically conductive polymer of claim 18, wherein each R is independently selected from the group consisting of thiophene, pyrrole, pyridine, and aniline.

20. A method of making a thermochromic material, comprising:

selecting a compound of the formula:

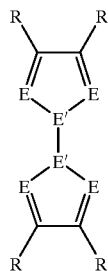

wherein
each E is independently selected from the group consisting of N, P, and As;
each E' is independently selected from the group consisting of P, As, Sb, and Bi; and
each R is independently selected from the group consisting of H, alkyl, aryl, dialkylamino, azide, alkoxy, dipnictaheteroles, polymerizable substituents, and disilylamino; and
crystallizing said compound.

21. A method of making a light-emitting diode, comprising:
selecting a compound of the formula:

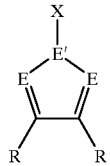

wherein
each E is independently selected from the group consisting of N, P, and As;
E'=Si or C(sp$^2$);
X represents at least one substituent wherein each substituent is independently selected from the group consisting of alkyl, aryl, dialkylamino, and alkoxy provided that X represents one substituent when E'=C(sp$^2$) and X represents two substituents when E'=Si;
each R is independently selected from the group consisting of H, alkyl, aryl, dialkylamino, azide, alkoxy, dipnictaheteroles, polymerizable substituents, and disilylamino;
dispersing said compound in a polymeric film;
placing a transparent anode on a glass substrate;
placing an electron donor layer on said transparent anode;
placing an electron transporting layer comprised of said compound dispersed in said polymeric film on said electron donor layer; and
placing a cathode on said electron transporting layer.

22. The method of claim 21, wherein said transparent anode is an indium tin oxide anode, said electron donor layer is comprised of p-phenylenevinylene, and said cathode is comprised of aluminum.

23. A method of making a molecular charge-transfer salt, comprising:
selecting a compound of the formula:

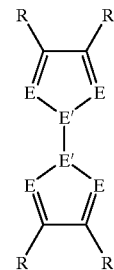

wherein
E'=C(sp$^2$) wherein a double bond is formed between E' and E';
each E is independently selected from the group consisting of N, P, and As; and
each R is independently selected from the group consisting of H, alkyl, aryl, dialkylamino, azide, alkoxy, dipnictaheteroles, polymerizable substituents, and disilylamino;
mixing said compound with an electron donor when E=N and mixing said compound with an electron acceptor when E=P or As so as to form a mixture;
co-crystallizing said mixture wherein said donors and said acceptors are stacked in a segregated stacking architecture so that there is an intermolecular electronic orbital overlap between adjacent donor and adjacent acceptors and wherein said donor undergoes partial oxidation and said acceptor undergoes partial reduction.

* * * * *